United States Patent
Su

(10) Patent No.: US 11,378,516 B2
(45) Date of Patent: Jul. 5, 2022

(54) LABEL-FREE SINGLE MOLECULE SPECTROSCOPY AND DETECTION

(71) Applicant: Arizona Board of Regents on Behalf of the University of Arizona, Tucson, AZ (US)

(72) Inventor: Tsu-Te Judith Su, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 92 days.

(21) Appl. No.: 16/765,810

(22) PCT Filed: Feb. 7, 2019

(86) PCT No.: PCT/US2019/017115
§ 371 (c)(1),
(2) Date: May 20, 2020

(87) PCT Pub. No.: WO2019/157223
PCT Pub. Date: Aug. 15, 2019

(65) Prior Publication Data
US 2020/0355611 A1    Nov. 12, 2020

Related U.S. Application Data

(60) Provisional application No. 62/627,521, filed on Feb. 7, 2018.

(51) Int. Cl.
*G01N 21/64* (2006.01)
*G02B 17/00* (2006.01)
(52) U.S. Cl.
CPC ....... *G01N 21/648* (2013.01); *G01N 21/6486* (2013.01); *G02B 17/004* (2013.01); *G02B 2207/101* (2013.01)

(58) Field of Classification Search
CPC ............ G01N 21/648; G01N 21/6486; G01N 21/552; G02B 17/004; G02B 2207/101; A61K 49/00; A61K 49/18; A61N 1/44
See application file for complete search history.

(56) References Cited

U.S. PATENT DOCUMENTS 7,630,417 B1    12/2009 Malek et al.
2005/0018203 A1    1/2005 Hogan
(Continued)

FOREIGN PATENT DOCUMENTS

EP    3370059 A1 *    9/2018    ......... G01N 21/6452

OTHER PUBLICATIONS

Shopova et al., Enhanced evanescent coupling to whispering-gallery modes due to gold nanorods grown on the microresonator surface, Appl Phys B (2008) 93: 183-187 DOI 10.1007/s00340-008-3180-6 (Year: 2008).*

(Continued)

*Primary Examiner* — Marcus H Taningco
(74) *Attorney, Agent, or Firm* — Venable LLP; Henry J. Daley

(57) ABSTRACT

A label-free detection and characterization system includes an optical source; an optical path arranged to be optically coupled to the optical source; an optical resonator disposed proximate the optical path along a side of the optical path, the optical resonator having an optical whispering-gallery mode and being optically coupled to the optical path through an evanescent field to excite the optical whispering-gallery mode; an optical receiver arranged to be optically coupled to the optical path. The optical source is frequency locked to a resonance frequency of the optical resonator and provides light sufficiently intense to provide four-wave mixing while being coupled with the optical resonator resulting in a comb spectrum received by the optical receiver. The comb spec- (Continued)

trum provides characteristic changes in the presence of a substance in contact with the optical resonator to provide detection and characterization of the substance.

20 Claims, 15 Drawing Sheets

(56) References Cited

U.S. PATENT DOCUMENTS

| | | | |
|---|---|---|---|
| 2008/0285606 A1 | 11/2008 | Kippenberg et al. | |
| 2009/0097516 A1* | 4/2009 | Maleki | H01S 5/065 372/26 |
| 2011/0139970 A1* | 6/2011 | He | G01N 21/7746 250/227.18 |
| 2011/0235045 A1* | 9/2011 | Koerner | G01B 9/02057 356/451 |
| 2011/0255094 A1* | 10/2011 | Mohageg | G01C 19/72 356/461 |
| 2012/0268731 A1* | 10/2012 | Zhu | G01N 21/7746 356/73 |
| 2012/0327497 A1* | 12/2012 | Matsko | G02F 1/0123 359/239 |
| 2013/0003766 A1* | 1/2013 | Savchenkov | G04F 5/14 372/38.01 |
| 2014/0192363 A1* | 7/2014 | Kippenberg | G01J 3/42 356/451 |
| 2015/0301034 A1 | 10/2015 | Su | |
| 2015/0355086 A1 | 12/2015 | Gagliardi et al. | |
| 2016/0084747 A1* | 3/2016 | Arnold | G01N 21/31 356/335 |
| 2016/0266110 A1 | 9/2016 | Ozdemir et al. | |
| 2016/0349177 A1* | 12/2016 | Iguchi | G02F 1/3532 |
| 2018/0306696 A1* | 10/2018 | Ozdemir | G01N 15/1434 |
| 2020/0006912 A1* | 1/2020 | Lancaster | H01S 3/1307 |
| 2020/0355611 A1* | 11/2020 | Su | A61N 1/44 |

OTHER PUBLICATIONS

Borgia et al., "Single-molecule studies of protein folding", Annu. Rev. Biochem., 2008, vol. 77, pp. 101-125.

Campos et al., "Aphotoprotection strategy for microsecond-resolution single-molecule fluorescence spectroscopy", Nature Methods, 2011, vol. 8, No. 2, pp. 143-146.

Kippenberg et al., "Microresonator-based optical frequency combs", Science, 2011, vol. 332, No. 6029, pp. 555-559.

Lindorff-Larsen et al., "How fast-folding proteins fold", Science, Oct. 2011, vol. 334, No. 6055, pp. 517-520.

So much more to know. Science, 309(5731):78-102, 2005.

Su et al., "Label-free detection of single nanoparticles and biological molecules using microtoroid optical resonators", Light: Science & Applications, 2016, vol. 5, No. 1, p. e16001.

Su, "Label-free single exosome detection using frequency-locked microtoroid optical resonators", ACS Photonics, 2015,vol. 2.No. 9, pp. 1241-1245.

Suh et al., "Microresonator soliton dual-comb spectroscopy", Science, 2016.

Vollmer et al., "whispering-gallery-mode biosensing: label-free detection down to single molecules", Nature Methods, vol. 5, No. 7, Jun. 27, 2008, pp. 591-596, entire document [online] URL <https://www.researchgate.net/publication/5267253_ Whispering-Gallery-Mode_Biosensing_Label-Free_Detection_Down_to_Single_ Molecules> DOI:10.1038/NMETH.1221>.

\* cited by examiner

LABEL-FREE SINGLE MOLECULE SPECTROSCOPY AND DETECTION

CROSS-REFERENCE TO RELATED APPLICATIONS

The present patent application is a National Stage Application under 35 U.S.C. § 371 of International Application No. PCT/US2019/017115, filed on Feb. 7, 2019, which claims priority benefit to U.S. Provisional Patent Application No. 62/627,521, filed on Feb. 7, 2018, the entire content of which are incorporated herein by reference. All references cited anywhere in this specification, including the Background and Detailed Description sections, are incorporated by reference as if each had been individually incorporated.

BACKGROUND

1. Technical Field

The field of currently claimed embodiments of this invention relates to label-free spectroscopy and detection of a substance, and more particularly, but not limited to, label-free single molecule spectroscopy and detection.

2. Discussion of Related Art

The current inventor has recently developed a label-free biological and chemical sensing system known as a frequency locked optical whispering evanescent resonator (FLOWER) that integrates microtoroid optical resonators with frequency locking feedback control, which aids the suppression of noise. FLOWER (U.S. Pat. No. 9,737,770), is currently capable of highly sensitive detection down to the single macromolecule level, as demonstrated by label-free detection of single human interleukin-2 (IL-2) molecules. To date, FLOWER has achieved a signal to noise ratio of 5 using an anti-IL-2 antibody layer immobilized on a microtorrid to specifically capture IL-2. However, this approach does not provide spectroscopy for identification as well as detection. Therefore, there remains a need for improved label-free spectroscopy and detection systems and methods.

SUMMARY OF THE DISCLOSURE

An aspect of the present disclosure is to provide a label-free detection and characterization system. The system includes an optical source; an optical path having a first end and a second end, the optical path arranged to be optically coupled to the optical source at the first end; an optical resonator disposed proximate the optical path along a side of the optical path between the first and second ends, the optical resonator having an optical whispering-gallery mode and being optically coupled to the optical path through an evanescent field to excite the optical whispering-gallery mode; and an optical receiver arranged to be optically coupled to the second end of the optical path. The optical source is frequency locked to a resonance frequency of the optical resonator and provides light sufficiently intense to provide four-wave mixing while being coupled with the optical resonator resulting in a comb spectrum received by the optical receiver. The comb spectrum provides characteristic changes in the presence of a substance in contact with the optical resonator to provide detection and characterization of the substance.

In an embodiment, the system further includes a reference detection and characterization system arranged to be in electrical communication with the data processor, the reference detection and characterization system being free of contact with the substance.

In an embodiment, the reference detection and characterization system includes: a second optical source; a second optical path having a first end and a second end, the second optical path arranged to be optically coupled to the second optical source at the first end; a second optical resonator disposed proximate the second optical path along a side of the second optical path between the first and second ends, the second optical resonator having a second optical whispering-gallery mode and being optically coupled to the second optical path through an evanescent field to excite the second optical whispering-gallery mode; and a second optical receiver arranged to be optically coupled to the second end of the second optical path. The second optical source is frequency locked to a resonance frequency of the second optical resonator and provides light sufficiently intense to provide four-wave mixing while being coupled with the second optical resonator resulting in a second comb spectrum received by the second optical receiver. The second comb spectrum provides a reference for comparison to the first mentioned comb spectrum.

BRIEF DESCRIPTION OF THE DRAWINGS

The present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

The term "light" is intended to have a broad definition that can include light in the visible as well as non-visible regions of the electromagnetic spectrum. For example, the term "light" can include, but is not limited to, visible, infrared and ultraviolet light. Similarly, the term "optical" has a corresponding broad definition as with the term "light".

An embodiment of the current invention incorporates FLOWER with dual frequency comb spectroscopy for molecular identification as well as detection. An embodiment of the current invention provides a label-free biological and chemical sensing system known as a frequency locked optical whispering evanescent resonator (FLOWER) that integrates microtoroid optical resonators with frequency locking feedback control which aids the suppression of noise. An embodiment of the invention is to incorporate FLOWER with dual frequency comb spectroscopy for molecular identification as well as detection. The inventors improved the signal to noise ratio of these measurements to greater than 1000 times using frequency locking feedback control in combination with innovative data processing techniques.

However, the general concepts of the current invention are not limited to only the use of FLOWER with dual frequency comb spectroscopy for molecular identification as well as detection.

Figure 1:
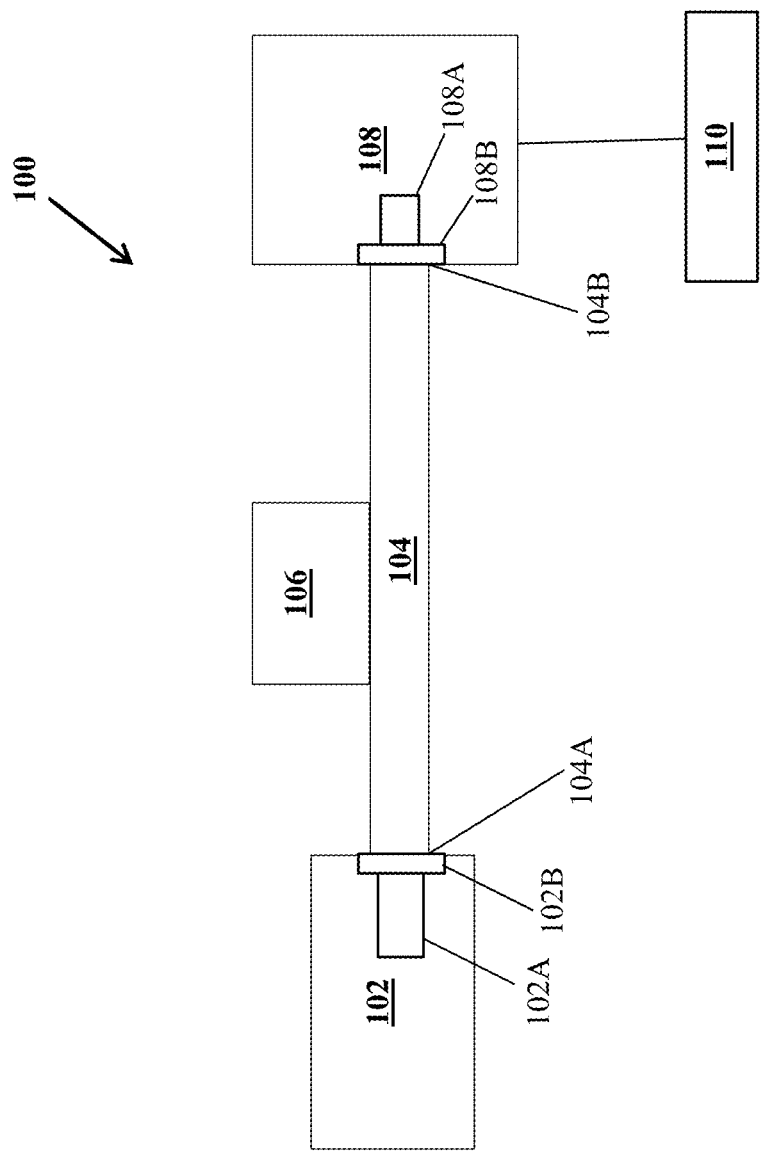
FIG. 1 is a schematic illustration of a label-free detection and characterization system, according to an embodiment of the present invention.

FIG. 1 is a schematic illustration of a label-free detection and characterization system 100, according to an embodiment of the present invention. Label-free detection and characterization system 100 includes an optical source 102 that is frequency locked to an optical cavity/resonator 106; an optical path 104 having a first end 104A and a second end 104B, the optical path 104 arranged to be optically coupled to the optical source 102 at the first end 104A; an optical cavity/resonator 106 disposed proximate the optical path 104 along a side of the optical path 104 between the first end 104A and the second end 104B, the optical resonator 106 having an optical whispering-gallery mode and being optically coupled to the optical path 104 through an evanescent field to excite the optical whispering-gallery mode; and an optical receiver 108 arranged to be optically coupled to the second end 104B of the optical path 104. For example, the optical path 104 can be substantially tangential to an optical path within the optical resonator 106 in some embodiments. However, the general concepts of the current invention are not limited to this example.

The term "characterization of the substance" can include, but is not limited to, identifying a type or species of a substance that is in contact with the optical resonator. In some embodiments, it can include, but is not limited to, identifying a shape or other physical configuration of a substance that is in contact with the optical resonator. These are non-limiting examples of the term "characterization of the substance."

The optical source 102 is frequency locked to a resonance frequency of the optical resonator 106 and provides light sufficiently intense to provide four-wave mixing while being coupled with the optical resonator 106 resulting in a comb spectrum that is received by the optical receiver 108. The comb spectrum provides characteristic changes in the presence of a substance in contact with the optical resonator 106 to provide detection and characterization of the substance.

In some embodiments, the optical source 102 includes a laser 102A and an optical amplifier 102B arranged at least one of between the laser and the first end 104A of the optical path 104 or integral with the optical path 104 along a portion thereof.

In some embodiments, the optical receiver 108 includes an optical detector 108A and an optical filter 108B arranged between the second end 104B of the optical path 104 and the optical detector 108A. The optical filter 108B substantially blocks or attenuates light at a transmitting wavelength from the laser 102A.

The substance detected and characterize according to some embodiments of the current invention can be at least one of a molecule, a virus, a portion of a virus, a biological cell, a portion of a biological cell, a microorganism, a portion of a microorganism, a particle, chemical compound, or any combination thereof.

In some embodiments, the label-free detection and characterization system 100 can further include a data processor 110 arranged to be in electrical communication with the optical receiver 108.

The optical resonator 106 can be, but is not limited to, a micro-toroidal optical resonator. The optical path 104 can be, but is not limited to, at least one of a free-space optical path, an optical waveguide, an optical fiber, an angled optical fiber or a prism. The optical filter can be, but is not limited to, a notch filter.

In some embodiments, the label-free detection and characterization system 100 can further include a reference detection and characterization system arranged to be in electrical communication with the data processor 110. The reference detection and characterization system is free of contact with the substance.

Figure 2:
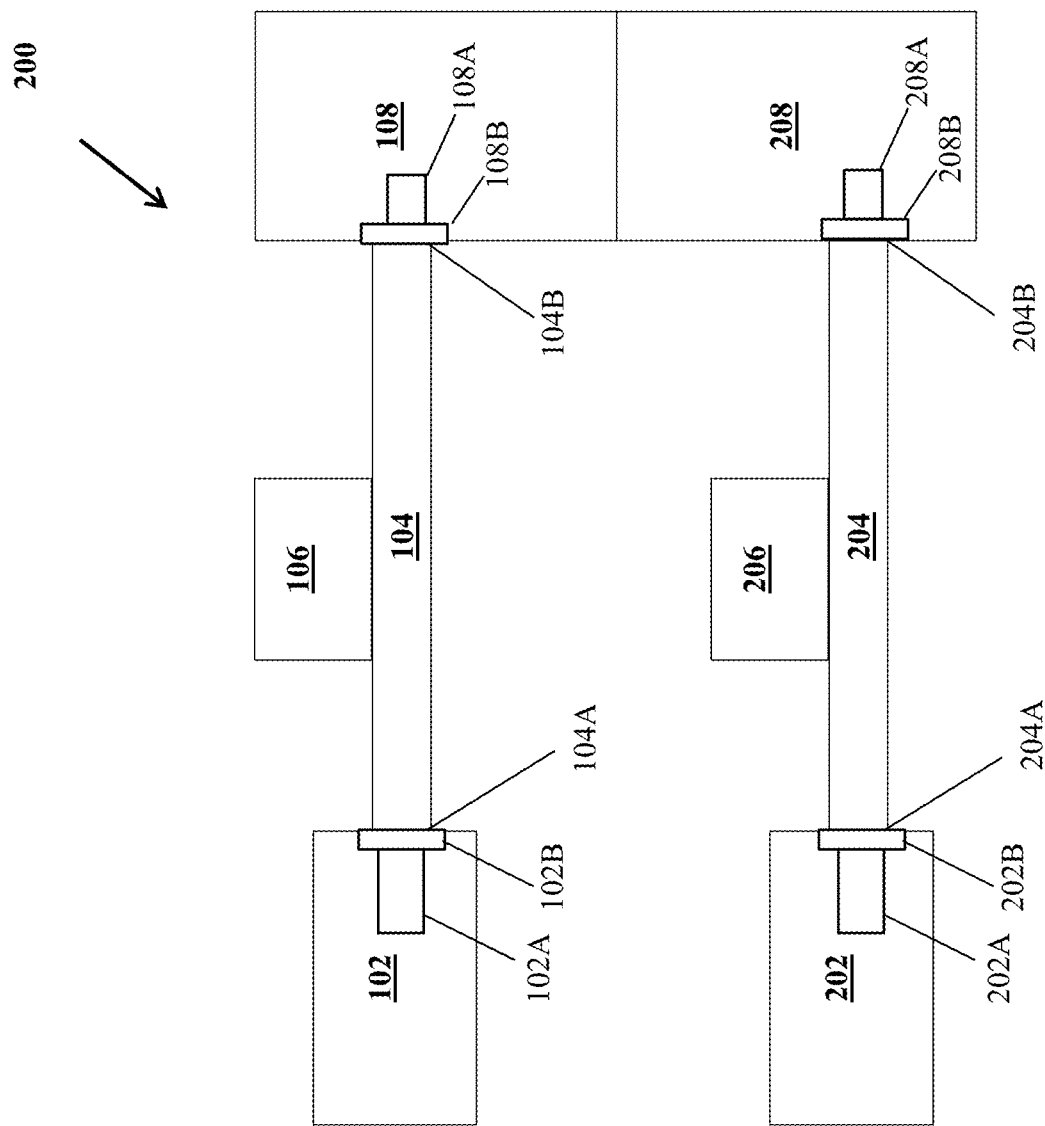
FIG. 2 is a schematic illustration of label-free detection and characterization system that further includes a reference detection and characterization system, according to another embodiment of the present invention.

FIG. 2 is a schematic illustration of label-free detection and characterization system 200 that further includes a reference detection and characterization system, according to an embodiment of the present invention. The components in FIG. 2 that have the same reference numerals as in FIG. 1 can be the same, or similar structures in some embodiments.

The reference detection and characterization system according to some embodiments can include, but is not limited to, a second optical source 202; a second optical path 204 having a first end 204A and a second end 204B, the second optical path 204 arranged to be optically coupled to the second optical source 202 at the first end 204A; a second optical resonator 206 disposed proximate the second optical path 204 along a side of the second optical path 204 between the first end 204A and the second end 204B, the second optical resonator 206 having a second optical whispering-gallery mode and being optically coupled to the second optical path 204 through an evanescent field to excite the second optical whispering-gallery mode; and a second optical receiver 208 arranged to be optically coupled to the second end 204B of the second optical path 204. The second optical source 202 is frequency locked to a resonance frequency of the second optical resonator 206 and provides light sufficiently intense to provide four-wave mixing while being coupled with the second optical resonator resulting in a second comb spectrum received by the second optical receiver. The second comb spectrum provides a reference for comparison to the first mentioned comb spectrum and for generating a radiofrequency beat spectrum.

The second optical source 202 includes a second laser 202A and a second optical amplifier 202B arranged at least one of between the second laser 202A and the first end 204A of the second optical path 204 or integral with the second optical path 204 along a portion thereof.

According to some embodiments, the second laser 202A and the first-mentioned laser 102A emit light at substantially the same wavelength, and the second optical resonator 206 and the first-mentioned optical resonator 106 have substantially the same resonances. In some embodiments, the second optical resonator 206 is a micro-toroidal optical resonator. In some embodiments, the second optical path 204 can be at least one of a free-space optical path, an optical waveguide, an optical fiber, an angled optical fiber or a prism.

In some embodiments, the second optical receiver 208 includes second optical detector 208A and second optical filter 208B arranged between the second end 204B of the second optical path 204 and the second optical detector 208A. The second optical filter 208B substantially blocks or attenuates light at a transmitting wavelength from the second laser 202A. In some embodiments, the second optical filter 208B can be a notch filter. In some embodiments, the first-mentioned optical whispering-gallery mode and the second optical whispering-gallery mode are substantially equal.

A large number of current biomedical and environmental problems would benefit from portable, rapid, sensitive, and accurate means to identify key microscopic, nanoscopic, or molecular markers specific to the problem. As one example, the detection of cancer could involve markers at all three of these length scales: the identification of abnormalities at the microscale in cell morphology via histopathologic imaging; the screening for nanoscopic extracellular vesicles (exosomes) secreted by cancer cells; and the detection of circulating mutated DNA. In addition, water quality monitoring, malaria, Alzheimer's disease, and cancer in general also present similar opportunities for screening based on tests that operate at a variety of length scales. In many cases, the current gold standard for diagnosis or detection of pathogens is based on imaging, such as histopathology of a biopsy in cancer, the observation of beta-amyloid plaques in Alzheimer's disease, or the observation of the *Plasmodium falciparum* parasite that causes malaria. Imaging provides a wealth of information that enables low false-positive rates; however, its diagnostic and prognostic ability can be enhanced by sensing technologies that can detect markers at the nanoscopic and molecular levels. The "big picture" of the present disclosure is to use the most sensitive sensing technologies in concert with imaging techniques to investigate fundamental biological processes and to provide more accurate and earlier detection of disease or potentially harmful environmental conditions.

The inventors developed a label-free biological and chemical sensing system called frequency locked optical whispering evanescent resonator (FLOWER) that integrates microtoroid optical resonators with frequency locking feedback control, which aids the suppression of noise.

Figure 3:
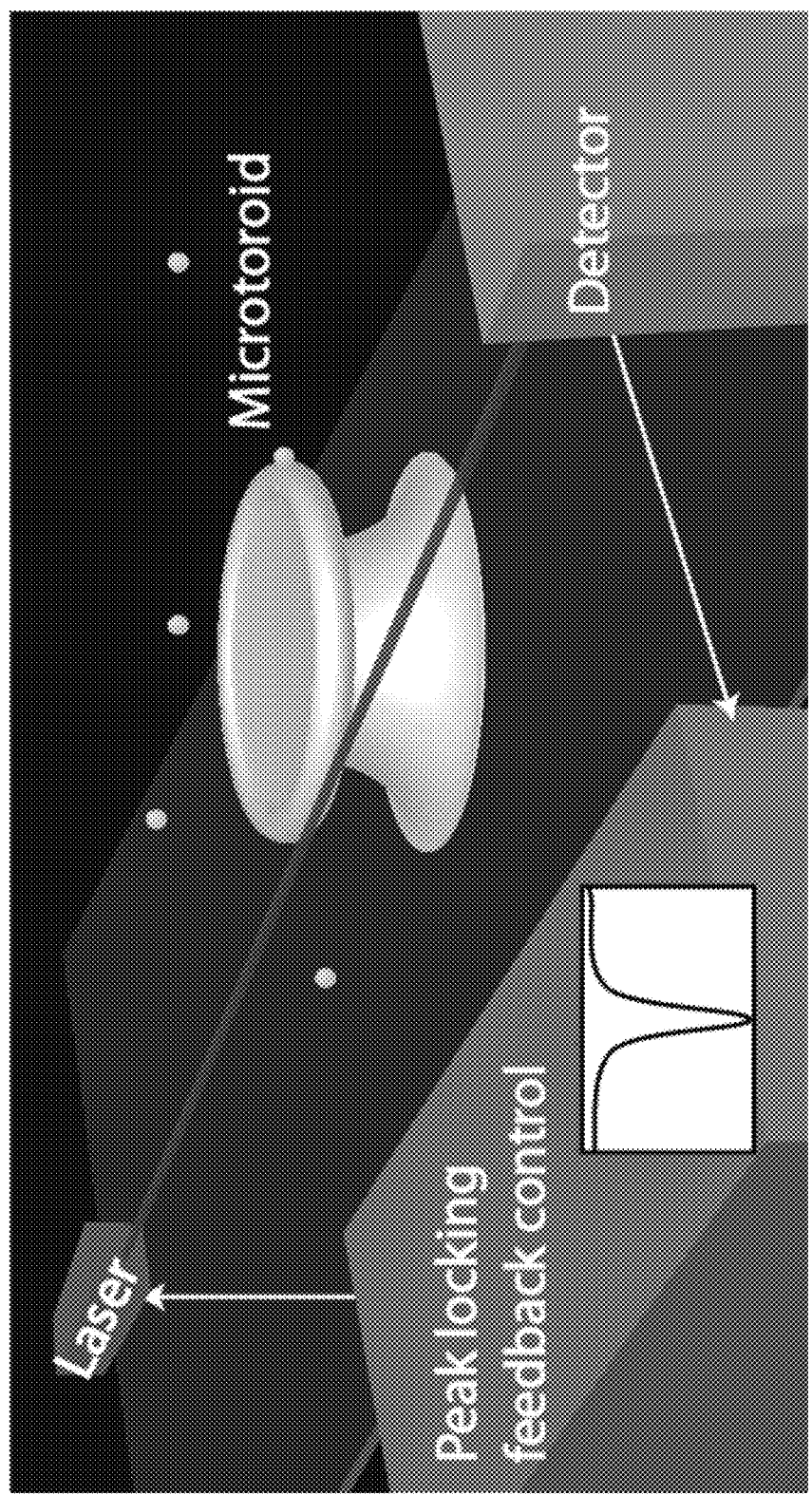
FIG. 3 depicts a schematic diagram of the Frequency locked whispering evanescent resonator (FLOWER) system, according to an embodiment of the present invention.

FIG. 3 depicts a schematic diagram of the Frequency locked whispering evanescent resonator (FLOWER) system, according to an embodiment of the present invention. FLOWER is based on microtoroid optical resonator technology. Light from a light source (e.g., a laser) is evanescently coupled into the microtoroid using an optical fiber (bold line). As particles bind the resonance frequency of the microtoroid changes, enabling sensitive detection of binding events. FLOWER is capable of highly sensitive detection down to the single macromolecule level, as demonstrated by label-free detection of single human interleukin-2 (IL-2) molecules. FLOWER can have a signal to noise ratio of 5 using an anti-IL-2 antibody layer immobilized on a microtoroid to specifically capture IL-2. A comparison of FLOWER with other label-free biosensing techniques can be made.

Figure 4:
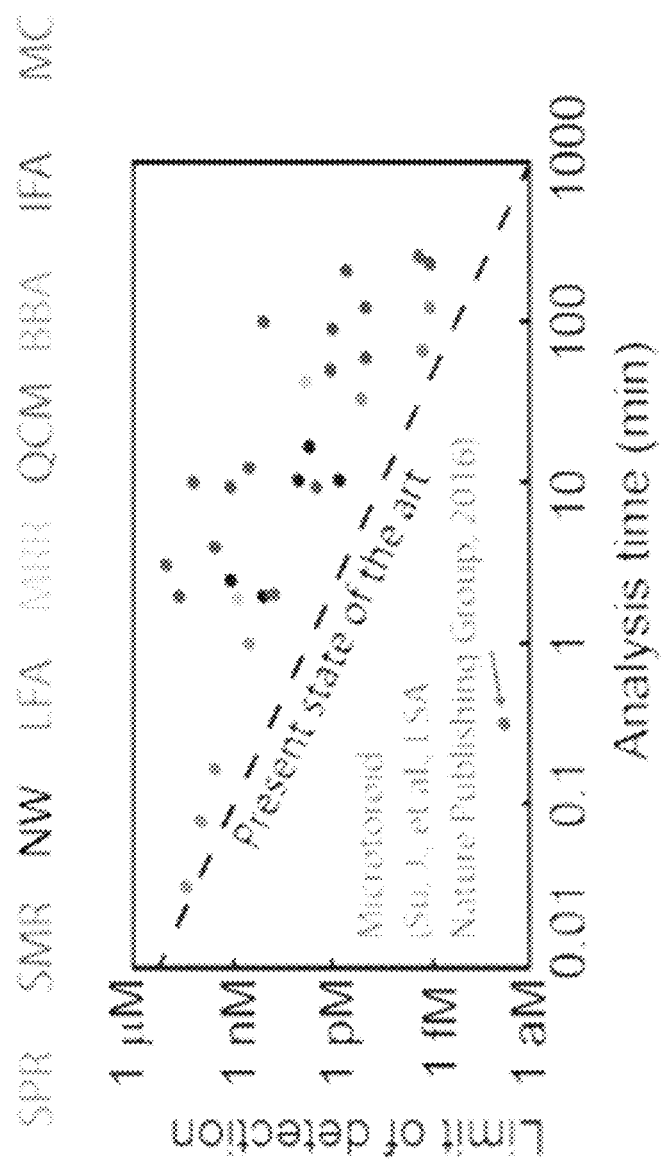
FIG. 4 shows a limit of detection versus analysis time for various known label-free biosensing techniques including microtoroid, according to an embodiment of the present invention.

FIG. 4 shows a limit of detection versus analysis time for various known label-free biosensing techniques including microtoroid. SPR corresponds to Surface Plasmon Resonance. SMR corresponds to Suspended Microchannel Resonators. NW corresponds to Nanowires. LFA corresponds to Lateral Flow Assay. MRR corresponds to Microring Resonator. QCM corresponds to Quartz Crystal Microbalance. BBA corresponds to BioBarcode Assay. IFA corresponds to Immunofluorescence Assay. MC corresponds to Microcantilever. According to an embodiment of the present invention, FLOWER with dual frequency comb spectroscopy can be incorporated to provide molecular identification as well as detection to examine the structure, dynamics, and mechanism of protein folding, for example.

FLOWER is based on microtoroid optical resonator technology. Microtoroid optical resonators operate based on light circulating inside a glass device (toroid). Because these devices are made of glass they can be functionalized to allow for the specific attachment of "bait" molecules. When analyte molecules bind to the "bait" this causes a change in the index of refraction near the device, which in turn alters the resonance frequency. These devices have enhanced sensitivity because as the light circulates, the light re-interrogates the bound analyte many times (up to 250,000 times for high quality devices).

Figures 5A, 5B, 5C:
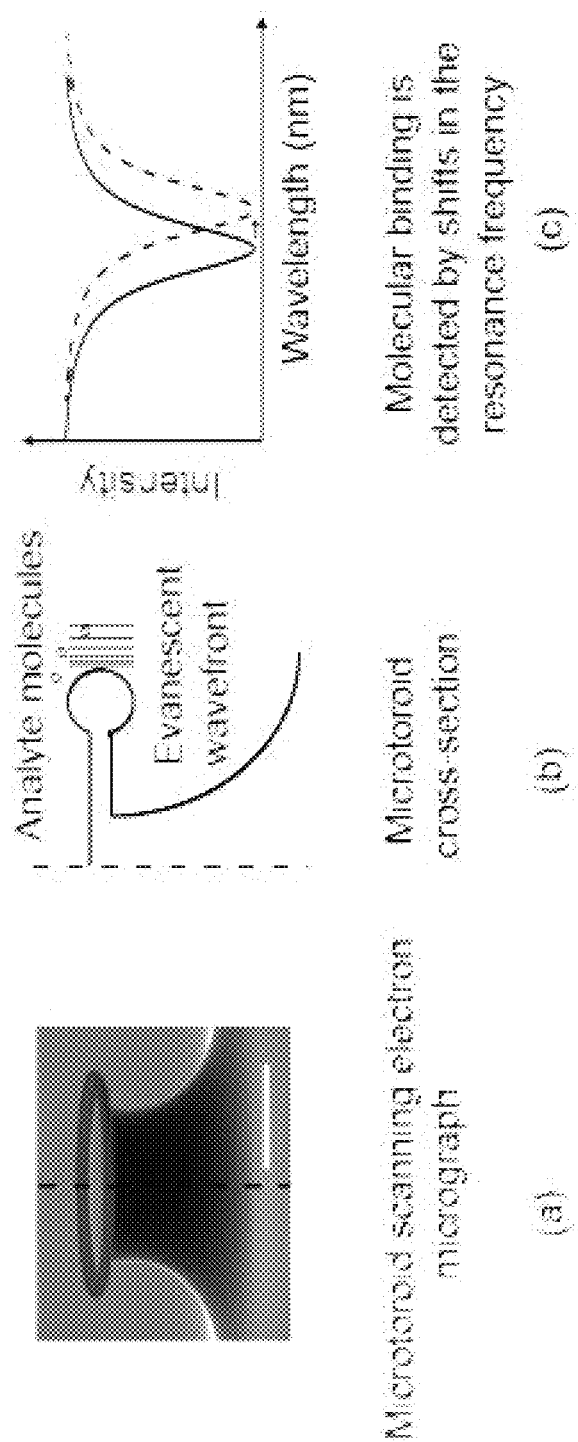
FIG. 5A shows a scanning electron micrograph (scale bar is 50 microns), according to an embodiment of the present invention.
FIG. 5B shows a schematic of an evanescent wavefront interacting with molecules near the microtoroid (not to scale), according to an embodiment of the present invention.
FIG. 5C shows the resonance shift (intensity vs. wavelength) due to molecules binding to a toroid's surface of the microtoroid, according to an embodiment of the present invention.

FIG. 5A shows a scanning electron micrograph (scale bar is 50 microns), according to an embodiment of the present invention. FIG. 5B shows a schematic of an evanescent wavefront interacting with molecules near the microtoroid (not to scale), according to an embodiment of the present invention. FIG. 5C shows the resonance shift (intensity vs. wavelength) due to molecules binding to the toroid's surface, according to an embodiment of the present invention. Whispering gallery mode resonators provide enhanced sensitivity as light interacts with the analyte molecules multiple times.

Microtoroids have the benefit as being extremely sensitive allowing the potential for detection down to the single molecule level. This allows for obtaining statistics of unitary events as opposed to having to look at an ensemble average. Microtoroids also do not require fluorescent tags, thus eliminating artifacts due to bleaching, blinking, and the presence of the tag. Because data can be obtained in the microsecond time regime continuously over several seconds or more, microtoroids have the potential to bridge a variety of time and length scales. In addition, the signal to noise ratio of these measurements can be improved to more than 1000 times using frequency locking feedback control in combination with innovative data processing techniques. This approach enables the detection of a wide range of nanoscale objects ranging from nanoparticles with radii spanning 100 nm to 2.5 nm to exosomes, ribosomes, and single protein molecules (160 kDa and 15.5 kDa). It is noted that microtoroids are different from microring (ring) resonators which are closed looped waveguides on a chip. Unlike a microring resonator, the microtoroid is on a pedestal, meaning that the evanescent field emanating from the microtoroid will not be scattered due to interaction with the underlying substrate. This characteristic, combined with a heat reflow process to eliminate lithographic blemishes and other surface imperfections, enables significantly longer photon confinement times and, in turn, sensitivity to lower concentrations of analyte to be measured with microtoroid resonators than with microring resonators.

Figure 6:
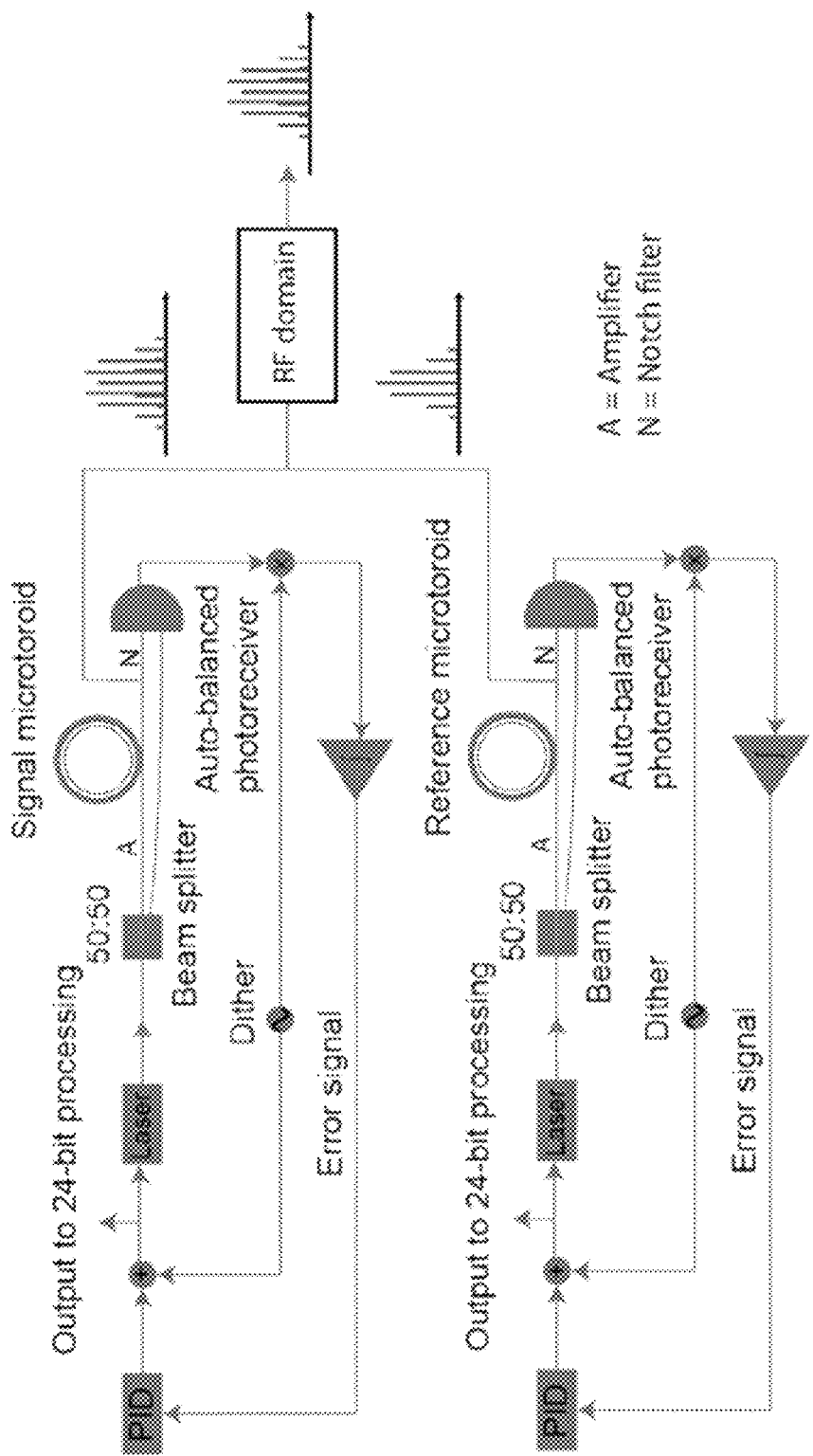
FIG. 6 shows a block diagram of Frequency Locked Optical Whispering Evanescent Resonator Spectroscopy (FLOWERS), according to an embodiment of the present invention.

FIG. 6 shows a block diagram of FLOWERS, according to an embodiment of the present invention. FLOWERS combines the high sensitivity detection capabilities of FLOWER with dual comb frequency spectroscopy. In this embodiment, two modified FLOWER systems are used, one is a reference system, and the other is a sensing system which interacts with the analyte of interest. An amplifier is added to each FLOWER system in order to enable frequency comb generation. In an embodiment, each FLOWER system can also include an optical amplifier and a notch filter. The optical amplifiers can be placed before each toroid so as to provide enough optical pump power such that four wave mixing occurs, resulting in frequency comb generation spanning an octave. Four wave mixing is the simultaneous absorption of two photons and the emission of two photons of different frequencies.

The notch filters are placed before each photoreceiver so that the feedback mechanism of FLOWER keeps the pump laser locked to the microtoroid resonance, even though the desired output is a now a frequency comb, instead of the transmission dip that is observed in our previous FLOWER experiments. The notch filters are adapted to remove wavelengths within a few nanometers of the pump wavelength (for example, 633 nm, or 560 nm depending on the protein of interest). When the pump is matched to a resonance of the microtoroid, a large bandwidth comb is generated with significant power outside of the notch filter bandwidth, and the photoreceiver measures a strong signal. However, if the pump laser and microtoroid fall out of resonance (for example, due to the binding of biological molecules or temperature drifts), then no frequency comb is generated. As a result, the pump laser is not efficiently coupled to the microtoroid, and most of the pump is just transmitted through the fiber, past the microtoroid, which is then ultimately blocked by the notch filter. Therefore, with the notch filter in place, the power measured on the photodiode can be used to determine whether the pump is on-resonance or off-resonance. Tracking these power changes enables tracking binding events. In order for the dual-comb spectroscopy approach to work, microtoroid resonators of slightly different but very close sizes can be used. This creates a beat frequency which can be measured in the radiofrequency (RF) domain, where it is easier to measure waveforms than in the optical domain. This output enables absorption spectroscopy to be performed.

Figure 7:
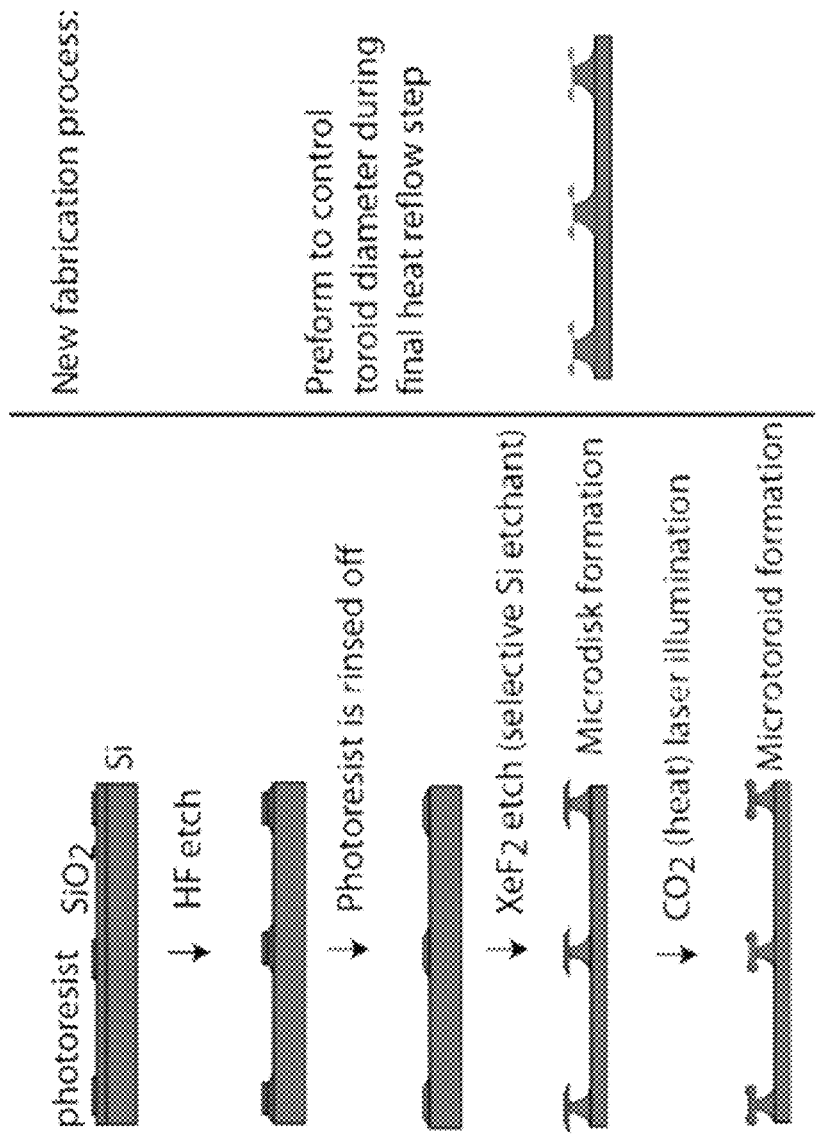
FIG. 7 depicts a flow diagram showing the various steps of a method or a process for fabricating toroids, according to an embodiment of the present invention.

Precise microfabrication of toroids is accomplished by using an annular preform which is precisely fabricated using a two-step lithography and etching procedure. FIG. 7 depicts flow diagram showing the various steps of a method or a process for fabricating toroids, according to an embodiment of the present invention. Microtoroid resonators of precise diameters needed for dual frequency comb spectroscopy are created using an annular preform created by two lithography and etching steps. A $CO_2$ laser is used to fire-polish the toroids giving them an extremely smooth surface finish which enables long photon confinement times. The $CO_2$ laser reflow melts the thicker silicon dioxide regions and stop at the thinner portion.

This system differs from chemical frequency sensing comb systems in that the analyte is brought in contact with the resonator. A benefit of having the analyte interact directly with one of the toroids is that it is possible to measure the optical properties and kinetics of single molecules binding to the signal toroid, in addition to overall concentration measurements. This is due to the microtoroid's evanescent field extending into the surrounding environment. Other microresonator geometries, such as wedge or microdisk resonators have modes that are well-confined within the disk, and thus may have a reduced or minimal interaction between the light and the surrounding environment. In order to characterize our system, FLOWER/FLOWERS is used, for example, to obtain the absorption spectra of a series of azo dyes whose absorption spectra are pH dependent, e.g. methyl orange and azo violet. Once it is demonstrated that absorption spectra can be obtained using FLOWER/FLOWERS, the absorption spectra of tyrosine side-groups change as proteins undergo conformational changes on the microtoroid can be further investigated. These experiments are described below.

The present system can be used to investigate how proteins fold and function. Proteins are a basic unit of life and their structure dictates their function. Determining the way an amino acid sequence folds into a functional three-dimensional protein structure is a major unsolved challenge. Understanding how proteins fold may be important from a basic science standpoint and for preventing and treating diseases. Being able to form proteins of a specific structure and therefore function would enable therapies for cancer, diabetes, prion diseases, Huntington's, and Alzheimer's diseases. Protein conformation can play an important role in how a protein functions. This is because the way a protein is folded affects how chemically reactive groups on the proteins surface are presented to the environment. This dictates, for example, how a binding site is created. Additionally, it is important to study conformational changes of folded proteins as they work together to effect biological function. Because of the limited and differing data from different techniques, protein folding theories have proven difficult to validate. Experiments often require high concentrations of proteins, models to interpret the data (e.g., fluorescence correlation spectroscopy which measures fluctuations in fluorescent intensity of molecules diffusing in a small volume), very stable configurations (e.g., nuclear magnetic resonance, x-ray crystallography), high forces (e.g., atomic force microscopy and in some cases optical tweezers), or non-physiologically relevant conditions (e.g., time resolved electron microscopy). Other techniques such as fluorescence resonance energy transfer (FRET) can require the use of more than one tag or require labels that can be difficult to generate for specific proteins. A concern is that the size of the label (tag, or bead as is used with optical tweezers) can affect the kinetics and stability of the protein being studied. In addition, fluorescent tags have limited stability under light and molecules rapidly diffuse out of their detection volume in a few milliseconds, thus preventing longer time experiments. Fluorescent tags also generate artifacts due to blinking and bleaching. To date single molecule FRET experiments have been able to examine equilibrium populations of molecules, but have only obtained limited success with measuring rates of reactions.

On the other hand, FLOWER/FLOWERS can be used to obtain single molecule, label-free (no fluorescent tags), microsecond time resolution protein folding data in order to reveal how proteins fold and function. For example, three problems can be investigated using FLOWER/FLOWERS. For example, initially, a well-defined transition can be studied, with many molecules at once, and then move up to more complex transitions involving fewer numbers of molecules. In order to study the simultaneous folding of many proteins (simple, two state transition, the mechanism of folding of the many proteins at once can be studied, by initially selecting a relatively simple and known protein with known folding and unfolding rates. An example of a relatively simple and known protein is insulin and actin. The protein can then be bound to a surface of the microtoroid, and the folding/unfolding of the protein synchronized with a pH change, at first. Then, the protein can be excited with a laser to induce a temperature change so as to determine whether the observed folding and unfolding rates are similar to known rates. Several proteins that fold across different time scales can be investigated in this way. Eventually, when the point where sub-states and fast time scales is reached, the results can be compared a simulation. In addition, the absorption spectra of tyrosine containing proteins as a function of pH can also be investigated.

Another goal of using FLOWER/FLOWERS is to investigate motor proteins walking on the surface of the toroid. Motor proteins are an attractive system to study using the microtoroid as the proteins undergo relatively large scale (8 nm step size) conformational changes as the protein walk. These proteins can be important as they are responsible for fundamental processes such as cell division and migration. For example, kinesin protein walking on the surface of the microtoroid can be investigated by binding microtubules to the toroids surface and adding Guanosine-5'-triphosphate (GTP) to initiate switching behavior. As the motor protein changes conformation, interactions with the toroid vary. It is expected that this interaction can induce changes in the index of refraction that can be detected as discrete events on the toroid. To ensure a large initial detection signal, a high number (e.g., 1000) of bound motor proteins can be investigated, initially, and then the number bound proteins can be decreased gradually to 100, 10, and eventually one, to see what characteristics persist. These experiments can enable correlating a well-studied system with the sensor response. In addition, unlike motor protein manipulation experiments using optical tweezers, the binding of a relatively large bead to the protein, which may perturb the kinetics, is not needed.

Another goal of FLOWER/FLOWERS is to study the conformational changes of a ribosome undergoing translation. Ribosomes are large (approximately 25 nm in diameter) and well within the detection capabilities of the FLOWER/FLOWERS system. Studying translation may be important because it is the second step in the central dogma of molecular biology. Translation is the process by which ribosomes plus transfer RNA (tRNA) decode messenger RNA (mRNA) to create an amino acid sequence that will fold into a three-dimensional protein structure. Prior structural studies have generated snapshots of this process. However, because translation is a very dynamic process, it is difficult to examine a single ribosome undergoing translation in real time. To cure this deficiency, the present FLOWER/FLOWERS system is used and a low concentration of mRNA is bound to a surface of a microtoroid to recruit or attract ribosomes and tRNA to that site, and the translation of tRNA is observed. Many labs have detailed the components needed to initiate translation in vitro.

A robust, extremely sensitive, and portable device using FLOWER/FLOWERS can be used to reveal fundamental biological processes. The device can be provided to an EMT or a solder to allow them to rapidly detect toxins, as well as markers of disease or pathology. The device can be used as a low cost system for the detection of viruses and bacteria in drinking water or food. The device can empower citizen scientists to monitor their drinking supply or breathing air. Furthermore, the device can be easily translatable to other labs, enabling robust assays for drug library screening, cell signaling studies, and clinical assays. Eventually, the device can be made available in drug stores throughout the country, creating a convenient, inexpensive, routine, accessible, and non-invasive means to impact the diagnosis and treatment of many diseases for which markers exist or are being sought.

In some embodiments, a single molecule spectroscopy system is provided to solve the problem of waterborne pathogen detection. The present system has a limit of detection significantly better than the current state of the art. In addition, the present system has greater identification capabilities, and achieves close to zero false negatives. For example, cyanobacteria, also known as blue-green algae, are found in bodies of water throughout the world. These bacteria harm the ecosystem and produce toxins that when ingested, inhaled, or touched, can adversely affect the nervous system, liver, kidneys, heart, cause cancer, male infertility, and even cause death. Therefore, it is of great interest to detect cyanobacteria and the toxins they produce in, for example, drinking supply and water recreation areas. The current limit of detection for these bacteria is approximately 10 to 50 cells per milliliter. Because bacteria grow exponentially, even a small quantity of cyanobacteria can quickly become a problem. A more sensitive detector would enable the presence of these bacteria to be detected earlier, and would make it easier to determine small concentration gradients and hence the source of the bacteria. More sensitive cyanotoxin detectors are therefore also needed. The sensing FLOWER system is capable of detecting individual protein molecules at a concentration of one part in a quadrillion (0.001 pg/mL). FLOWERS (Frequency Locked Optical Evanescent Resonator Spectroscopy) which incorporates FLOWER with dual frequency comb spectroscopy molecular identification as well as detection can be used for this purpose. In addition, FLOWERS can be also be combined with selective surface chemistries to create a robust cyanobacteria and cyanotoxin sensor for improved drinking and recreational water quality monitoring. For example, this system enables more precise environmental monitoring by significantly decreasing current limits of detection and providing improved identification capabilities. In addition, this system can significantly advance the field of whispering gallery mode optical biosensing by (1) providing molecular fingerprinting using dual frequency comb spectroscopy and (2) making robust whispering gallery mode sensors which are re-usable, easily calibrated, and benchmarked against existing technologies.

One of the main goals of the World Health Organization is that "all people, whatever their stage of development and their social and economic conditions, have the right to have access to an adequate supply of safe drinking water." Recently there has been a focus on developing effective platforms to detect pathogens in water. Cyanobacteria are 3.5 billion years old and grow in bodies of water throughout the world. They are adapted to harsh, low nutrient, low light environmental conditions and are quite hardy. Certain cyanobacteria and their toxic secretions, known as cyanotoxins, are poisonous to animals and humans.

Figure 8:
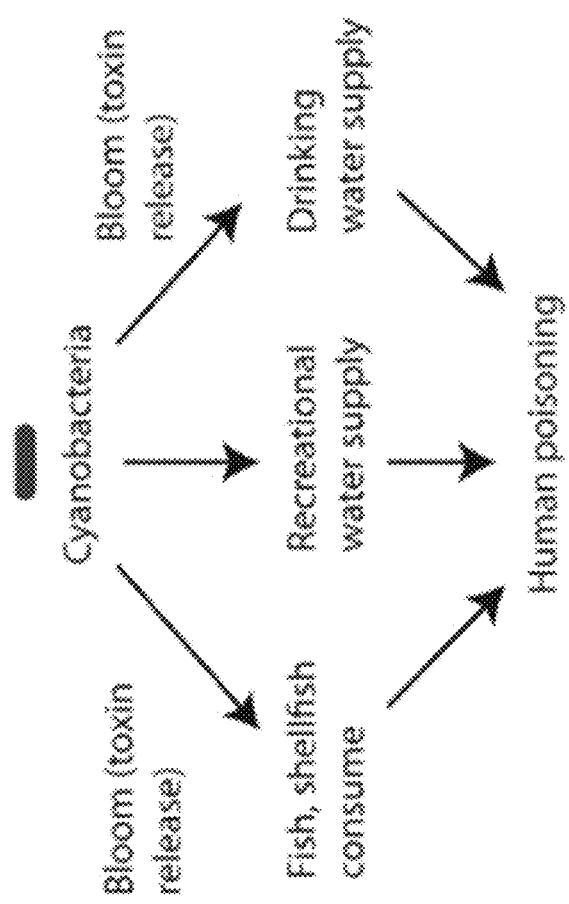
FIG. 8 is a flow diagram showing the various routes how cyanobacteria affect human health, according to an embodiment of the present invention.

FIG. 8 is flow diagram showing the various routes how cyanobacteria affect human health, according to an embodiment of the present invention. When cyanobacteria multiply, some strains release harmful cyanotoxins, which when ingested, inhaled, or touched can be harmful to humans and animals. In addition, cyanobacteria can alter the ecosystem by consuming resources needed for other plants and by changing oxygen levels in rivers and lakes. Drinking water or eating fish or shellfish that have been contaminated with cyanobacteria can cause illness or death. Water from cyanobacteria-contaminated areas may unknowingly be sprayed on crops, adsorbing to the crops, and poisoning the people who eat them. In addition, cyanotoxin aerosols caused by water crop spraying or recreational watersports can be inhaled by humans. Cyanobacteria can poison multiple levels of a food chain. For example, animals may eat plant roots contaminated by cyanobacteria, and it has been shown that when people subsequently consume those animals, they are at significantly higher risk of Parkinson's and Alzheimer's. Chronic exposure to low concentrations of cyanotoxins can also cause tumors. In cases of less poisonous species, cyanobacteria can cause unpleasant odors and taste and force additional chemical disinfectants such as copper sulfate or chlorine to be placed in water supplies. In addition, the removal of cyanobacteria from our drinking supply through membrane filtration or activated carbon can be costly. Due to the harm that cyanobacteria can cause both to humans and to the environment, there is a need for sensors that can detect and identify low concentrations of cyanobacteria and their toxins before they reach toxic levels. Common analytical methods of detecting cyanobacteria include conventional brightfield microscopy, quantitative Polymerase Chain Reaction (qPCR), enzyme-linked immunosorbent assay (ELISA), High-Performance Liquid Chromatography (HPLC), chlorophyll-A detection, protein phosphatase inhibition assay (PPIA), and mouse bioassay. The majority of these techniques are expensive and/or time consuming, requiring multiple steps, and in the case of the mouse bioassay, it requires a live animal. Assays such as chlorophyll-A also assume the presence of a toxin and cannot distinguish cyanobacteria from algae. The most sensitive of these techniques, qPCR has a limit of detection (LOD) of approximately $10^2$-$10^3$ cells/mL for cyanobacteria. In terms of cyanotoxin detection, ELISA has demonstrated a sensitivity of ng/mL. Recently, millimeter-sized piezoelectric cantilevers were used to detect the cyanobacteria *Microcystis aeruginosa* by lysing the cells and measuring their 16S ribosomal RNA content. Ribosomal RNA content is detected as not all cyanobacteria are toxic. As such it is important to identify toxin producing genes. Using this approach, researchers were able to report a lower LOD of 50 cells/mL. Because bacteria grow exponentially, even a small quantity such as this can quickly turn into a large problem. For example, using the reported doubling time of *M. aeruginosa* of every 24 hours, this translates into a billion cells/mL in about 24.2 days or a little under a month. Because cyanotoxins are released in the exponential growth phase, detecting cyanobacteria before they multiply is important.

The FLOWER system which uses frequency locked microtoroid optical resonators to detect single unlabeled macromolecules can be used to detect an unlabeled single human-interleukin-2 molecule which has a mass of 0.002 attograms. Currently, the most sensitive means to detect cyanobacteria involves extracting and detecting 16S ribosomal RNA using millimeter-sized cantilevers. As mentioned above, this method gives a LOD of 50 cells/mL. It is estimated that FLOWER is capable of detecting 16S rRNA from a single bacterium based on the following calculation. From the literature, a single *E. coli* has 0.8 ag of 16S rRNA. Assuming a similar amount of 16S rRNA in cyanobacteria, FLOWER should be able to easily detect the 16S rRNA extracted from a single bacterium. In terms of cyanotoxin detection, it is estimated from previous data that FLOWER can detect approximately 4.6 fg/mL of Microcystin-LR. This is several orders of magnitude more sensitive than the current reported limit of 1 pg/mL. In addition, to being more sensitive, FLOWER eliminates the need to label the target molecule, thus providing a reduction in the complexity and cost when compared to other assays such as ELISA.

Figure 9:
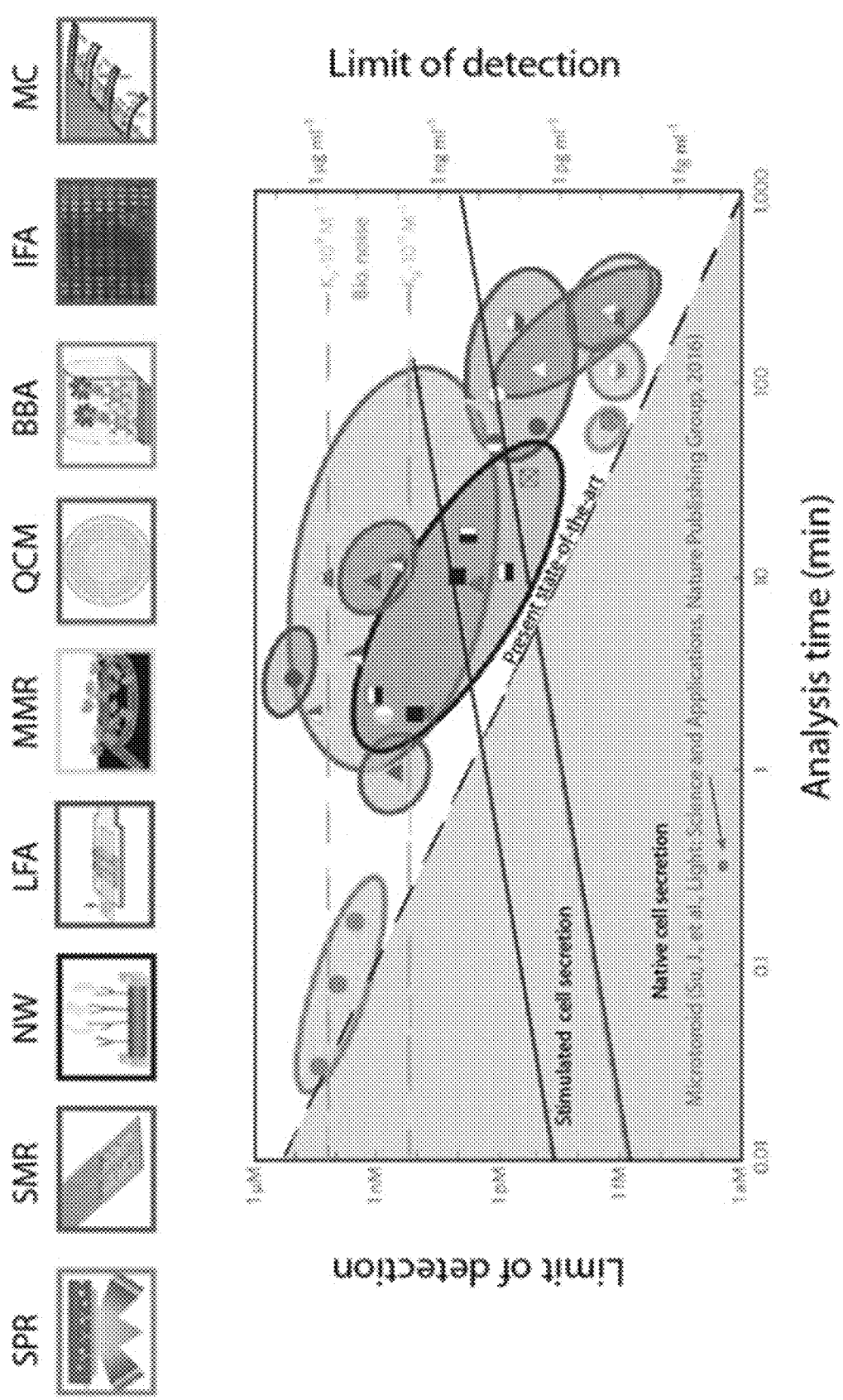
FIG. 9 is a plot of limit of detection (LOD) versus analysis time showing a comparison between various label-free biosensing techniques and the FLOWER system, according to an embodiment of the present invention.

Microtoroid optical resonators (shown in FIG. 5A) are extremely sensitive sensors. They are one of the most sensitive label-free detection techniques available, as shown in FIG. 9. Similar to FIG. 4, FIG. 9 is a plot of limit of detection versus analysis time showing a comparison between label-free biosensing techniques, according to an embodiment of the present invention. SPR corresponds to Surface Plasmon Resonance, SMR corresponds to Suspended Microchannel Resonators. NW corresponds to Nanowires. LFA corresponds to Lateral Flow Assay. MMR corresponds to Microring Resonator. QCM corresponds to Quartz Crystal Microbalance. BBA corresponds to BioBarcode Assay. IFA corresponds to Immunofluorescence Assay. MC corresponds to Microcantilever. FIG. 9 also shows the microtoroid data obtained using the present FLOWER system relative to the conventional techniques.

The benefit of using optical resonators such as the microtoroid is that they enable sensitive biodetection by measuring small refractive index changes without the need to label the target of interest. It is noted that microtoroids are different from microring (ring) resonators which are closed looped waveguides on a chip. Unlike the microring, the microtoroid is on a pedestal, meaning that the evanescent field emanating from the microtoroid will not be scattered due to interaction with the underlying substrate. This, combined with a heat reflow process to eliminate lithographic blemishes and other surface imperfections, enables significantly higher quality factors and, in turn, sensitivity to lower concentrations of analyte to be measured with microtoroid resonators than with microring resonators. Microtoroid optical resonators operate based on the principle of resonant recirculation of light. They are the optical analog of the acoustic whispering gallery. Acoustic whispering galleries were first described in the literature by Lord Rayleigh. He stood under the dome of St. Paul's Cathedral in London and noticed that whispers at one end of the dome could be heard 40 meters away at the other end of the dome because the sound waves were reflected along the walls of the dome with negligible loss. Optical resonators follow a similar principle, but use light instead of sound. Light is evanescently coupled into these glass devices and continuously totally internally reflects within them, generating an evanescent field (FIG. 5B and FIG. 10).

Figure 10:
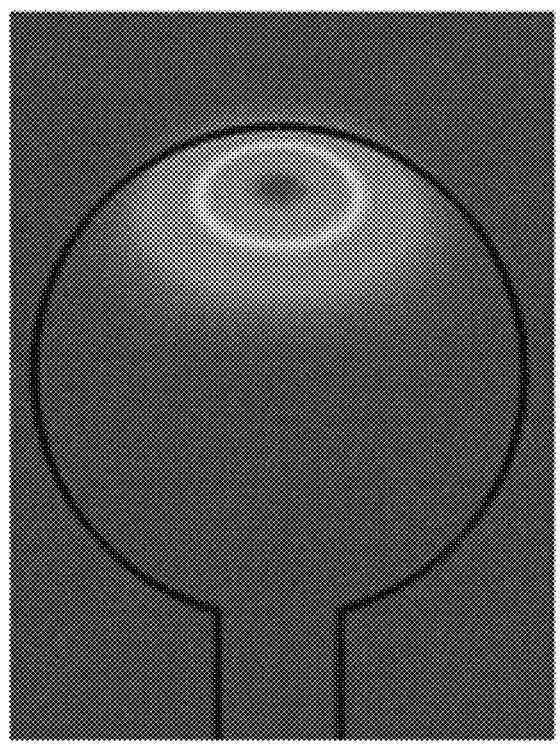
FIG. 10 shows a finite element COMSOL simulation of the capacitive Poynting energy density inside a silica microtoroid with major and minor diameter of 90 and 4 microns, respectively, according to an embodiment of the present invention.

FIG. 10 shows a finite element COMSOL simulation of the capacitive Poynting energy density inside a silica microtoroid with major and minor diameter of 90 and 4 microns, respectively, according to an embodiment of the present invention. The view presented is of a cross-section of the microtoroid. The toroid has a dumbbell cross-section and is immersed in water. As shown in FIG. 10, part of the electric field evanesces beyond the rim of the microtoroid. This is the sensing region of the device and it is localized to the rim of the toroid. When a particle with a different refractive index (or polarizability) than the background medium enters the evanescent field, part of the light passes through the particle, changing the optical path length of the light and decreasing the frequency at which the toroid resonates. This enables sensitive monitoring of particle binding events (FIG. 5C). Because light circulates multiple times within the device before exiting, it interacts multiple times with a particle, making the microtoroid a more sensitive sensor than a traditional single pass device such as a planar waveguide. Other optical resonators such as microrings have demonstrated picomolar sensitivities for protein detection, but have not been able to detect single molecules. Microspheres have been shown capable of detecting single Influenza A virus particles but not single protein molecules. Recently, gold nanoshells and nanorods are adhered to the surface of microspheres to create small plasmonic enhanced sensing hotspots for detecting proteins and DNA. However, such hotspots greatly reduce the sensing capture area of the device. The ideal situation would involve detection of proteins using the large surface area inherent to a bare resonator such as a toroid that is ~100 microns in diameter, which has thousands of times more capture area than a nanoparticle. The FLOWER system that integrates microtoroid optical resonators with frequency locking feedback control, suppressing noise is currently capable of highly sensitive, label-free detection down to the level of a single, 14.4 kDa protein molecule.

Figure 11:
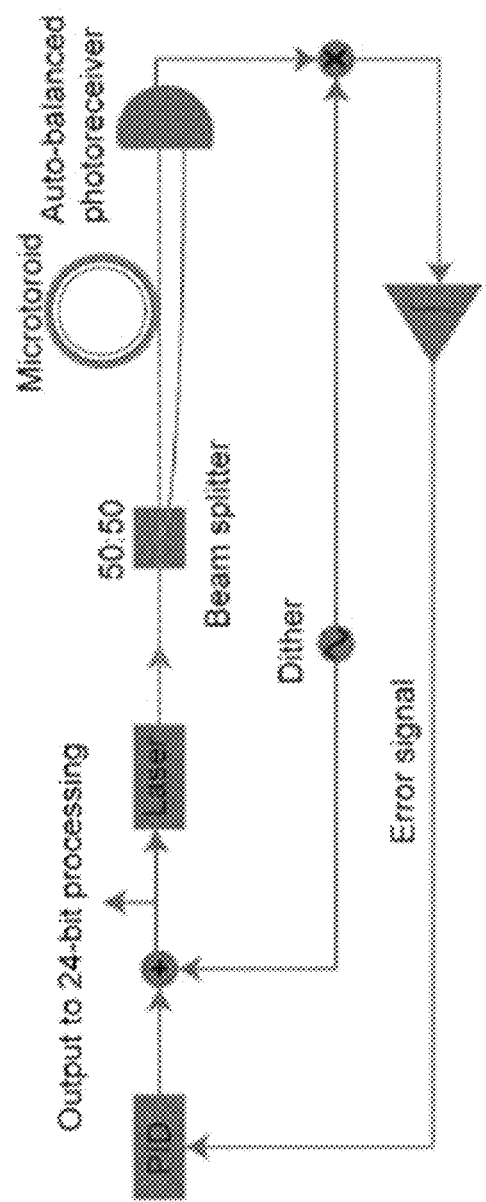
FIG. 11 shows a block diagram of the FLOWER system, according to an embodiment of the present invention.

FIG. 11 shows a block diagram of the FLOWER system, according to an embodiment of the present invention. In the FLOWER system, a small high-frequency dither is used to modulate the driving laser frequency. When multiplied by the toroid output and time-averaged, this dither signal generates an error signal whose amplitude is proportional to the difference between the current laser frequency and resonant frequency. This error signal is sent to a PID controller whose output is used to set the laser frequency, thus completing the feedback loop. A computer records the observed frequency shifts.

Figures 12A, 12B, 12C:
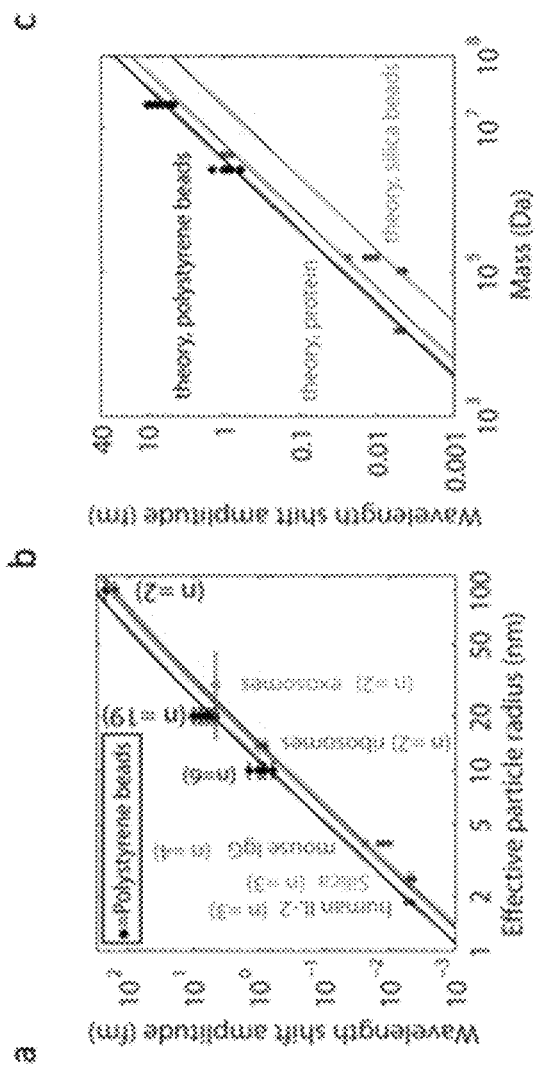
FIG. 12A-12C show theoretical comparison of results with experimental data over several orders of magnitude of particle size, according to embodiments of the present invention.

FIG. 12A-12C show theoretical comparison of results with experimental data over several orders of magnitude of particle size, according to an embodiment of the present invention. FIG. 12A shows that wide range of particle sizes with radii from 2-100 nm are detected. For human IL-2 and mouse IgG, an effective particle radius was calculated based on spheres having the same molecular weights as the individual molecules. The solid lines are theoretical predictions based on the different dielectric constants of the particles being detected. Errors bars represent the known polydispersity of samples. FIG. 12B shows a maximum wavelength shift as a function of molecular weight for the same particles as shown in FIG. 12A. The experimental data points agree well with theoretical predictions based on first order perturbation theory for different materials (solid lines). FIG. 12C show the resonance wavelength shift (trace) over time of the microtoroid as polystyrene latex nanoparticles 10 nm radius bind to the microtoroid's surface. As a nanoparticle binds, the resonance frequency of the toroid changes. This change appears as a 'step' in the plot of resonance frequency shift over time. The step-fit is shown as a dashed line. The inset in FIG. 12C is a zoom-out of the toroid response over the full recording range of 10 seconds.

As individual particles bind, the wavelength at which the microtoroid resonates increases, thus generating a step-like curve over time. In addition to being able to detect biomolecules and particles in pure solutions, FLOWER has other benefits in real-world sensing tasks. FLOWER is capable of sensitive detection of bioparticles in complex solutions such as mouse serum. FLOWER is capable of detecting individual exosomes (nanovesicles) in serum at a dilution of one to one million in saline. As well as being sensitive, FLOWER also has a fast sensor response time of under 30 seconds. As FLOWER requires no exogenous labels, FLOWER can reduce complexity and cost compared to other biosensing techniques. FLOWERS or Frequency Locked Optical Whispering Evanescent Resonator Spectroscopy which is an extension of FLOWER can further significantly improve the water quality monitoring field by offering unprecedented, ultra-sensitive detection and identification of cyanobacteria and their secreted toxins.

As described in the above paragraphs, the FLOWER approach can be extended to combine two FLOWER systems to create dual frequency combs, which will enable absorption spectroscopy to be performed, as shown in FIG. 6. As stated above, each FLOWER system is modified to include an optical amplifier and a notch filter. The optical amplifiers are placed before each toroid in order to provide enough optical pump power such that four wave mixing occurs, resulting in broad spectral range frequency comb generation. Four wave mixing is the simultaneous of absorption of two photons and the emission of two photons of different frequencies. The notch filters are placed before each photoreceiver so that the feedback mechanism of FLOWER keeps the pump laser locked to the microtoroid resonance, even though the desired output is a now a frequency comb, instead of the transmission dip that we observed in our previous FLOWER experiments. The notch filters are configured to remove wavelengths within a few nanometers of the pump wavelength of the laser (approximately 633 nm). When the pump is matched to a resonance of the microtoroid, a large bandwidth comb can be generated with significant power outside of the notch filter bandwidth, and the photoreceiver can measure a strong signal. However, if the pump laser and microtoroid fall out of resonance (for example, due to the binding of biological molecules or temperature drifts), then no frequency comb is generated, the pump laser is not efficiently coupled to the microtoroid, and most of the pump is just transmitted through the fiber, past the microtoroid, and is then ultimately be blocked by the notch filter. Therefore, with the notch filter in place, the power measured on the photodiode can be used to determine whether the pump is on-resonance or off-resonance. Tracking these power changes enables tracking binding events.

In some embodiments, in order for the dual-comb spectroscopy approach to work, microtoroid resonators of slightly different but very close sizes are used. This creates a beat frequency to be created which can be measured in the radiofrequency (RF) domain. This output enables absorption spectroscopy to be performed. Precise microfabrication of toroids can be done by using an annular preform which is precisely fabricated using a two-step lithography and etching procedure.

Figure 13:
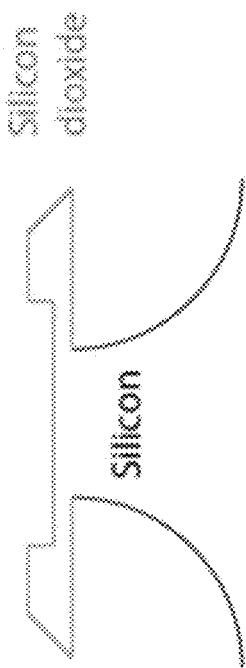
FIG. 13 shows a cross-section of a microtoroid resonator, according to an embodiment of the present invention.

FIG. 13 shows a cross-section of a microtoroid resonator, according to an embodiment of the present invention. Microtoroid resonators of precise diameters needed for dual frequency comb spectroscopy can be created using an annual preform created by two lithography and etching steps. The $CO_2$ laser reflow melts the thicker silicon dioxide regions and stop at the thinner portion. This system differs from chemical frequency sensing comb systems in that the analyte is brought in contact with the resonator. One benefit of having the analyte interact directly with one of the toroids is that it is to be able to measure the optical properties and kinetics of single molecules binding to the signal toroid, in addition to overall concentration measurements. These benefits are possible because the microtoroid's evanescent field extends into the surrounding environment. Other microresonator geometries, such as wedge or microdisk resonators have modes that are well-confined within the disk, and thus have little interaction between the light and the surrounding environment. In an embodiment, FLOWERS can be used to obtain the absorption spectra of a rhodamine B test sample, for example. Experiments can be performed for varying concentrations (micromolar to attomolar) of rhodamine B.

In an embodiment, FLOWERS can also be used to detect bacteria, such as but not limited to, cyanobacteria. Sensing cyanobacteria is sometimes preferable to direct sensing of cyanotoxins, as cyanotoxin immunoassays suffer from low antibody avidity. As such, cyanobacteria assays are developed that involve detecting 16S ribosomal RNA (rRNA) from cyanobacteria using complementary DNA immobilized to the surface of a sensor. Cyanobacteria are a good example to perform dual comb spectroscopy on due to their blue-green color. Frequency-locked microtoroid optical resonators functionalized with a 100-base DNA fragment can be used to detect 16S ribosomal RNA (rRNA) extracted from the cyanobacteria *M. aeruginosa*. The length of the DNA fragment (~34 nm) is selected such that it is short enough to lie completely within the evanescent field of the microtoroid, but long enough to avoid steric hindrance. Finite element simulations are performed and show that the evanescent field of the microtoroid extends out about 200 nm. A DNA sequence, which is denoted as DS1 is used. The DNA sequence DS1 is shown to bind to the 16S rRNA of *M. aeruginosa*. Microtoroids are fabricated as described in the above paragraphs and *M. aeruginosa* is purchased from the University of Texas-Austin culture collection. 16S rRNA is extracted from *M. aeruginosa* cells following known procedures. DS1 is tethered to the glass surface of the microtoroid using chemistries previously developed for binding DNA to glass substrates. In this example, the surface of the microtoroid is primed for DNA adhesion using 3-aminopropyltriethoxysilane (APTES). In this example, vapor deposition rather than solution deposition is use for the depositing APTES as it is observed that vapor deposition is maintains the quality factor of the microtoroid devices. After functionalization with APTES, the succinylated DS1 sequence which can be obtained commercially is attached to the surface of the micritoroid. To confirm that DS1 is actually bound to the surface of the microtoroid, an experiment is performed where DNA that has a TEX 615 fluorophore (excitation wavelength at about 569 nm) is also bound on a distal end of DS1. The microtoroid is then imaged after binding has occurred using fluorescence microscopy. A control experiment is also performed where a microtoroid with DNA bound without a fluorophore is also imaged. After procedures are established to functionalize the toroid surface with DS1, the optimal surface coverage of DNA for which the greatest amount of 16S rRNA will bind is determined. This is performed by varying the surface coverage of DNA on the surface of the microtoroid in the presence of a saturating amount of rRNA and determining what concentration of DNA results in the largest resonance frequency shift during exposure to a flowing rRNA solution. To vary the DNA surface coverage, the concentration of capture DNA used in the immobilization reaction is varied while keeping the reaction time fixed. As small shifts in voltage/wavelength are recorded, data is recorded using a 24-bit data acquisition card. In an embodiment, initially, all 24-bits may not be needed as it is expected to see large shifts in wavelength due to saturating concentrations of 16S rRNA, but as lower concentrations are approached, a regime is reached where this may become important. In an embodiment, DNA and 16S rRNA solutions are flowed over the surface of the microtoroid using, for example, a syringe pump at 1 mL/min. Before experiments are run, all solutions are thermally equilibrated in a room temperature water bath for more than 1 hour. In an embodiment, on-chip temperature control of our resonators using a thermoelectric cooler may also be implemented. The concentration of 16S rRNA that can be detected with an optimized surface coverage of capture DNA can be determined.

Figure 14:
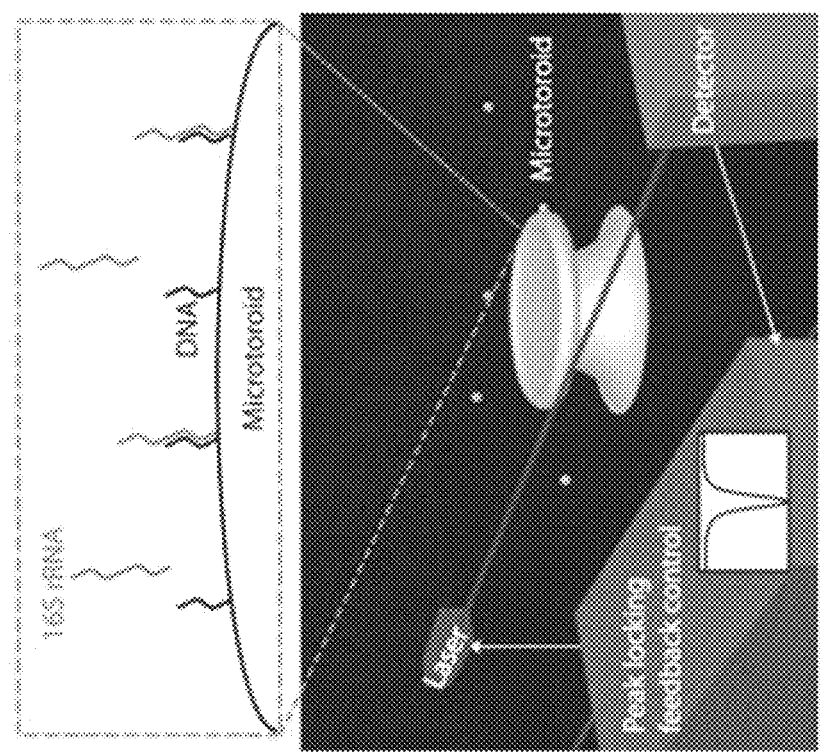
FIG. 14 shows a schematic diagram of the FLOWER system using the microtoroid, according to an embodiment of the present invention.

FIG. 14 show a schematic diagram of the FLOWER system using the microtoroid, according to an embodiment of the present invention. In an embodiment, the surface of the microtoroid is sensitized for detecting 16S rRNA from *M. aeruginosa*. DNA that targets a region of the 16S rRNA is immobilized on the surface of the toroid. To ensure that a signal is detected, a first measurement is performed of the resonance frequency shift of the microtoroid for a large (saturating) amount of rRNA from the extract from approximately 10,000 cells (i.e., a relatively large amount or concentration of cells). Once it is established that a signal is detected, the experiment is repeated for decreasing amounts of 16S rRNA diluted in phosphate buffered saline solution (PBS). Plotting the resonance frequency shift observed as a function of concentration will allow us to establish a standard curve, relating the concentration of 16S rRNA with observed frequency shift. The experiments can be also complemented with computational models. For example, a 2D axisymmetric finite element model of the optics of the microtoroid using COMSOL Multiphysics can be implemented. The finite element model allows computing the optical field strength both within the microtoroid and outside the microtoroid, within the evanescent zone. A benefit of such a numerical model is that the full 2D axisymmetric distribution of the evanescent field around the toroid can be quickly computed. Such a calculation would be difficult, if not impossible, to perform analytically. In addition to computation of the propagating and evanescent field strengths, such finite element models are capable of computing the eigenmodes of the system. These eigenmodes correspond to the resonant frequencies. By adding a small layer of material, in this case a layer of DNA+RNA to the numerical simulation, the shift in eigenmode (resonant frequency) we expect to see upon binding, assuming homogeneous coverage of the microtoroid, can be computed. Ultimately, the goal of these experiments is to quantify the number of cyanobacteria in a given sample. To achieve this goal, the concentration of 16S rRNA that is measure using the microtoroid is related to a concentration of cyanobacteria. In principle, this relationship can be established using only the microtoroid, as the total shift from the binding of the lysate of a large number of cells (approximately 10,000 cells) is measured to correlate resonance shift directly with cell concentration. Previous studies have also estimated the typical concentration of 16S rRNA in a single cell. However, in case there is variability between different populations of cyanobacteria, independent measurements of the concentration of 16S rRNA in the lysate are performed using known numbers of cells. These independent measurements are performed using Nanodrop UV-Vis spectroscopy. Nanodrop UV-Vis spectroscopy measures the absorbance of light as a function of wavelength for 1-2 microliters of samples. A concentration can then be determined using Beer's Law. Since a typical commercial Nanodrop UV-Vis spectroscopy system does not have the sensitivity to quantify the levels of 16S rRNA in a single cell, the measurements are instead performed on the lysate of 1000 cells and extrapolated downward. With all of these measurements robust correlation of the three quantities of interest (observed microtoroid resonance shift, concentration of 16S rRNA, and concentration of cyanobacteria) can be obtained.

Control experiments are also performed to quantify the level of non-specific binding of our system. This can be done, for example, for a "nonsense" strand of RNA of the same length as 16S rRNA. In addition, control experiments are also performed using lysate from bacteria that does not contain the target RNA. A response time of the sensor to this control sample is measured. In addition, the response when this sample is mixed with lysate containing increasing amounts of 16S rRNA is also measured. To further confirm that the resonance frequency shifts that are observed are from the 16S rRNA binding to the surface of the functionalized microtoroid, a procedure from the literature is adapted where a secondary binding assay is performed to confirm the binding of rRNA to a DNA-functionalized cantilever. In this experiment, a 50 nm gold nanoparticle is attached to another strand of DNA which targets the 16S rRNA of *M. aeruginosa* (FIG. 15).

Figure 15:
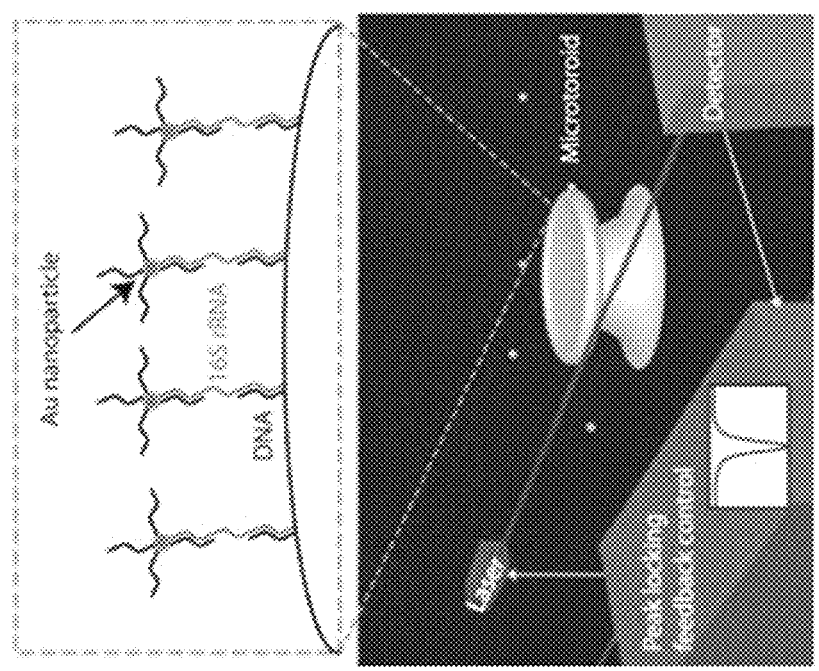
FIG. 15 depicts a schematic diagram of the FLOWER system using the microtoroid wherein the toroid's surface is sensitized for detecting 16S rRNA from *M. aeruginosa*, according to an embodiment of the present invention.
Figure 16:
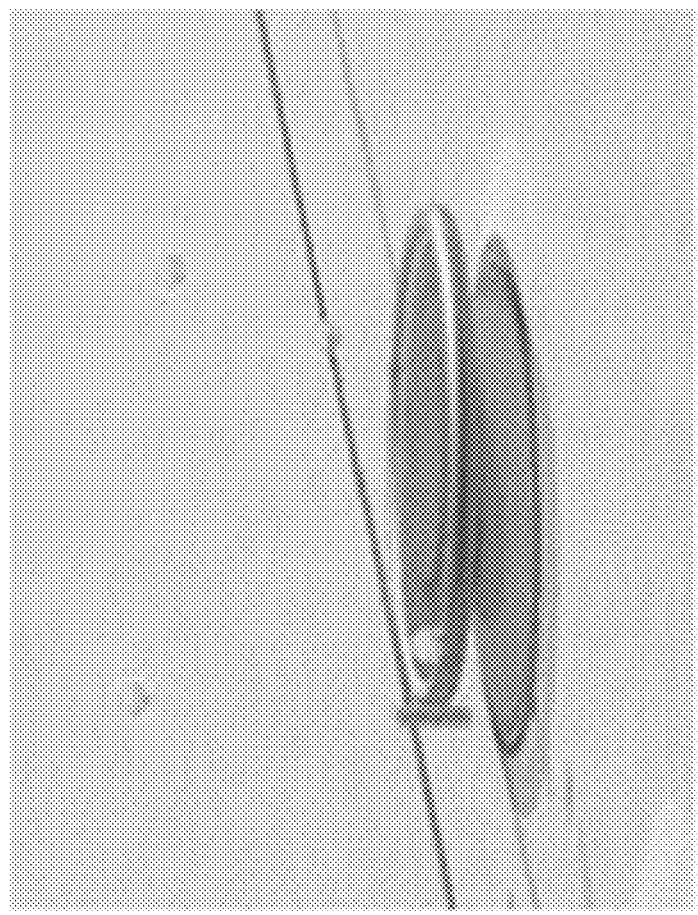
FIG. 16 depicts a three-dimensional illustration of microtoroid with a gold nanorod being bound to a surface of the microtoroid, according to an embodiment of the present invention.

FIG. 15 depicts a schematic diagram of the FLOWER system using the microtoroid wherein the toroid's surface is sensitized for detecting 16S rRNA from *M. aeruginosa*, according to an embodiment of the present invention. DNA that targets a region of the 16S rRNA is bound to the surface of the toroid. For further confirmation of binding, a secondary assay will be performed where a targeted strand of DNA with a gold nanoparticle attached is bound to the other end of the 16S rRNA. The DNA is synthesized with a thiol group in order to bind the gold nanoparticle. Due to the high polarizability of gold, an extremely large resonance shift occurs when this second DNA strand binds. The resonance frequency shift we observe can be compared with theoretical predictions of what is expect for a 50 nm gold particle entering the evanescent field of the microtoroid. In this case, it is assumed that the frequency shift from the secondary DNA sequence is negligible compared to the frequency shift that originates from a 50 nm gold nanoparticle. The shift upon binding of a particle is developed in 1945 and is known as the Bethe-Schwinger cavity perturbation formula:

$$d = 2a = 2\left(\frac{2V_m}{D}\frac{E_{0,max}^2}{E_0^2(r_s)}\right)^{1/3}\left(\frac{\Delta\lambda}{\lambda}\right)^{1/3},$$

where d is the diameter of a bound particle, a is the radius, $V_m$ is the electromagnetic mode volume of the microtoroid, D is a dielectric factor calculated from the index of refraction of the bound particle and the background solution, $E_{0,max}^2$ is the electric field intensity at the microtoroid equator, and $E_0^2(r_s)$ is the electric field at the microtoroid surface. $V_m$ and $E_{0,max}^2/E_0^2(r_s)$ are determined from finite element simulations.

After it is established that known concentrations of lysed cyanobacteria in diluted phosphate buffered saline solution can be detected, detecting an unknown concentration of cyanobacteria from a known contaminated water supply can then be implemented. In this case, for example, water from the Saguaro Lake in Arizona can be sampled. Cyanobacteria have previously been reported in the Saguaro Lake at concentrations of ng/L.30 Before the experiments are performed, it is first confirmed whether or not cyanobacteria are present in the sample, for example using conventional microscopy. Cyanobacteria have a long filamental structure which is several microns in diameter and around 60 microns in length. As such, they are easily visualized using a conventional light microscope when present in a sample at high concentration. In addition, for further confirmation, because cyanobacteria contain chlorophyll-A, they should have a significant amount of autofluorescence which should enable them to be seen under fluorescence microscopy. To detect an unknown concentration of cyanobacteria, a standard curve using known concentrations of 16S rRNA from *M. aeruginosa* is first generated. The concentration of a large amount of 16S rRNA using Nanodrop UV-Vis spectroscopy is measured and a serial dilutions in phosphate buffered saline dilution is performed. After generating the calibration curve, the temperature of the sample stage is increased using a Peltier heater in order to melt the hybridized 16S rRNA and refresh the toroid for a new experiment. In this manner, the same device may be re-used, eliminating signal uncertainty due to device variation and allowing calibration of the device to be performed prior to each experiment.

After the RNA is melted off of the DNA, a rinse step is performed, and a new 16S rRNA that has been extracted from the cyanobacteria is flowed in and the resulting resonance frequency shift is measured. The concentration of 16S rRNA and therefore the number of cells/mL present in the water via the standard curve is then determined. qPCR is also performed on these samples and the results compared with those obtained using FLOWERS.

In addition to establishing the LOD of the sensor and its dynamic range, the sensor response time is also evaluated by measuring how soon after injection it takes for the resonance frequency of the microtoroid to stabilize. The reversibility of our sensor is also assessed by repeatedly melting off the hybridized 16S rRNA and performing binding assays with the same known concentration of 16S rRNA on the same toroid in sequence. To evaluate whether FLOWERS works as a cyanobacteria characterization tool, we will attempt to use the absorption spectra generated by FLOWERS to distinguish between spiked filtered river water solutions of cyanobacteria (blue-green algae) and green algae, which is another algal phyla. Mixtures of cyanobacteria and green algae are also tested. These results will be compared to those obtained using a spectrophotometer as well as those reported in the literature.

An alternative to detecting RNA isolated from cyanobacteria is detection of the cyanotoxin produced by the bacteria. A FLOWERS sensor is created for the cyanotoxin, Microcystin-LR and its analytical performance is compared to the RNA sensor. Microcystin-LR is a small molecule (molecular weight ~1000 Da) and is considered one of the most potent cyanotoxins. It can damage the liver and is a potential carcinogen. Microcystin-LR solutions and monoclonal antibodies to Microcystin-LR can be purchased from Abraxis. Monoclonal antibodies for Microcystin-LR are covalently bound to the surface of the microtoroid using inventor's attachment protocols.

A series of experiments are performed to quantitatively determine the analytical performance parameters of the sensor. First, a saturating amount of anti-microcystin-LR is bound to the microtoroid and a large (picomolar) concentration of Microcystin-LR is flowed in. If this concentration can be detected, the concentration can be lowered by an order of magnitude. The concentration is lowed continuously until a signal cannot be distinguished from background. In these experiments, the resonance wavelength shift of the microtoroid as Microcystin-LR binds is recorded. Once it is established the LOD and dynamic range of the system for Microcystin-LR, the sensor response time can be determined as well. In addition, control experiments can also be performed using a mismatched antibody in order to quantify our degree of non-specific binding. Another control experiment which can be performed is using the antibody for Microcystin-LR but flowing in the ligand Dynorphin A instead. Dynorphin A is commercially available and has a similar molecular weight to Microcystin-LR but would not be expected to bind to Microcystin-LR. The reversibility characteristic of the sensor can also be tested to determine whether the sensor is reversible or not by using a chaotropic agent to regenerate the antibody.

The binding of Microcystin-LR to the microtoroid can be confirmed using a secondary binding assay. This procedure can be validated externally by ELISA prior to attempting on the sensor itself. After Microcystin-LR has bound, the number of bound molecules on the toroid can be estimated by dividing the total shift by the shift induced by a single binding event. The shift from a single binding event may either be measured experimentally, or it may be obtained from theory. Then, after the Microcystin-LR has bound, anti-Microcystin-LR is introduced at a moderately high concentration and the shift of the resonance is tracked. The total resonance frequency shift is equal the product of the number of initially bound Microcystin-LR molecules (which is computed) times the shift induced by the binding of a single anti-Microscystin-LR antibody, which again could be obtained from either experiment or theory. If this total shift agrees with the expected prediction, we can confirm that we are primarily tracking the binding of Microcystin-LR in the first step of this experiment. Control experiments may also be performed using a mismatched antibody to quantify a degree of non-specific binding.

Once it is established that solutions spiked with known concentrations of Microcystin-LR can be detected, a standard curve can be generated and progressed to seeing if unknown concentrations of Microcystin-LR from a contaminated source can be detected. Experiments are performed both with filtered and unfiltered samples. These experiments allow the determination how pure the samples need to be. It is noted that the size histograms allow distinguishing between groups of particles of different size providing another means of distinguishing contaminants from our analyte of interest. First, the presence of Microcystin-LR in these samples is confirmed using HPLC, for example. Once it is established that Microcystin-LR is present in these samples, a diluted solution containing these toxins can be flowed over the microtoroid and record the resonance frequency shift. A diluted solution is selected so as to prevent the quality factor of the resonator from decreasing such that binding events cannot be tracked. The shift that is detected in then compared with the standard curve to determine the concentration of Microcystin-LR in the sample.

Our results can then be compared with the results obtained from an indirect competitive ELISA assay. Experiments where Microcystin-LR is spiked into various type of liquid samples such as natural water and infant formula can be performed. In addition, to evaluate whether FLOWERS works as a cyanotoxin characterization tool, the measured absorption spectra can be used to distinguish between spiked filtered river water solutions of the cyanotoxins, Microcystin-LR and Microcystin-RR. These results can also be compared to those obtained using a spectrophotometer.

Finally, the combination of FLOWERS with plasmonic enhancement for additional sensitivity is implemented. FIG. 16 depicts a three-dimensional illustration of microtoroid with a gold nanorod being bound to a surface of the microtoroid, according to an embodiment of the present invention. Gold nanorods have been shown to have a 1000× electric field enhancement at their ends. This electric field enhancement will cause a corresponding increase in the signal to noise ratio of the device. Note that in FIG. 16 the gold nanorod is not drawn to scale. Although plasmonic hotspots decrease the capture area of the sensor, they provide enhanced sensitivity. Gold nanorods bound to the surface of a microsphere resonator were shown to have a 1000× increase in sensitivity due to the electric field enhancement at the ends of the rod. This enabled the detection of a binding event of an 8 bp strand of DNA. Therefore, in an embodiment, in order to enhance the detection efficiency of the present FLOWERS system, a 42 nm×12 nm citrate capped gold nanorods, for example, are functionalized using DNA targeted for the 16S rRNA of *M. aeruginosa*. One end of the DNA sequence has a thiol group in order to bind to the gold nanorod. It has previously been shown that gold nanoshells will adhere to small, randomly occurring manufacturing defects in microsphere optical resonators. Gold (Au) nanorods of the size indicated above are selected due to their wide availability and their known signal enhancement properties. A nanorod-containing solution is flowed over the microtoroid and determine whether this is a sufficient procedure to bind nanorods to the surface of the microtoroid. If this procedure does not work, the Au nanorod can be tethered to the toroid using a mercaptopropyl silane. The binding of the nanorod to the surface of the microtoroid can be confirmed using scanning electron microscopy (SEM).

After binding nanorods successfully, the optimal concentration of gold nanorods to use that will generate a likely binding event is determined empirically. The surface coverage of gold nanorods is minimized so that the quality factor of the FLOWERS device is not significantly degraded to the extent that a resonance peak cannot be tracked. Once it is determined the optimal concentration of functionalized nanorods to place on the surface of the microtoroid, the system is calibrated with silica beads of known size. Experiments for three different particle sizes: 50 nm, 10 nm, and 5 nm can be performed, for example. Silica beads are chosen as their index of refraction is on average close to that of biological particles. The beads are coated with a mercaptopropyl silane in order to promote attachment to the gold nanorods. In addition to varying the size of the beads, the concentration of the beads can also be varied. The resonance frequency shift of the microtoroid scales with the volume of the bead as well as with the concentration of the beads. Once the FLOWERS system is calibrated with beads, a saturating amount of 16S rRNA, extracted from ~10,000 cells is then flowed over the microtoroid. Using a large concentration ensures that a signal is detected. The concentration of 16S rRNA is then gradually decreased to determine the limit of detection (LOD). In these experiments, as before, the resonance frequency shift of the microtoroid over time is recorded as binding events occur. The sensor response time can be quantified by measuring the amount of time it takes for the toroid to reach steady state. To confirm that the resonance frequency shift that is observed is due to the binding of 16S rRNA to the DNA-functionalized gold nanorod, a secondary binding assay with another DNA strand that is targeted for 16S rRNA that has a 20 nm gold nanoparticle attached on one end is performed. A smaller diameter particle than before can be selected in case the combined signal shift from the gold nanorod plus the gold nanoparticle is too large for our feedback controller to track successfully. Similar to previous experiments, the experimental results can be compared with finite element simulations using COMSOL Multiphysics.

Control experiments can also be performed to ensure that the binding of 16S rRNA to the nanorod is observed. These experiment include flowing in a mistargeted RNA strand and quantifying the resulting resonance frequency shift. As in the prior experiments, in-situ calibration experiments can be performed by generating a standard curve for known concentrations of 16S rRNA. This enable determining whether an unknown concentration of 16S rRNA from water samples from a known contaminated source can be detected. In addition to the above control experiments, another type of control can further be implemented wherein a 10 nm gold nanoparticle is attached to the DNA instead of a 20 nm gold nanoparticle. This experiment is performed to determine whether to signal strength scales according to particle volume as one would expect if binding events are occurring. In addition to performing these experiments for cyanobacteria, these experiments can also be performed for the cyanotoxin Microcystin-LR. The gold nanorods can be functionalized with monoclonal antibodies for Microcystin-LR and experiments similar to those described in the above paragraphs can be performed. The results can be compared with the results obtained from ELISA.

REFERENCES

[1] Judith Su. Label-free single exosome detection using frequency-locked microtoroid optical resonators. ACS Photonics, 2(9):1241-1245, 2015.

[2] Judith Su, Alexander F G Goldberg, and BrianMStoltz. Label-free detection of single nanoparticles and biological molecules using microtoroid optical resonators. Light: Science & Applications, 5(1):e16001, 2016.

[3] T. J. Kippenberg, R. Holzwarth, and S. A. Diddams. Microresonator-based optical frequency combs. Science, 332(6029):555-559, 2011.

[4] Myoung-Gyun Suh, Qi-Fan Yang, Ki Youl Yang, Xu Yi, and Kerry J. Vahala. Microresonator soliton dual-comb spectroscopy. Science, 2016.

[5] So much more to know. Science, 309(5731):78-102, 2005.

[6] Bruce Alberts. Molecular Biology of the Cell. Garland Science, 2014.

[7] Kresten Lindorff-Larsen, Stefano Piana, Ron O. Dror, and David E. Shaw. How fast-folding proteins fold. Science, 334(6055):517-520, October 2011.

[8] Alessandro Borgia, Philip M Williams, and Jane Clarke. Single-molecule studies of protein folding. Annu. Rev. Biochem., 77:101-125, 2008.

[9] Luis A Campos, Jianwei Liu, Xiang Wang, Ravishankar Ramanathan, Douglas S English, and Victor Muñoz. A photo protection strategy for microsecond-resolution single-molecule fluorescence spectroscopy. Nature Methods, 8(2):143-146, 2011.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

I claim:

1. A label-free detection and characterization system, comprising:
    an optical source;
    an optical path having a first end and a second end, said optical path arranged to be optically coupled to said optical source at said first end;
    an optical resonator disposed proximate said optical path along a side of said optical path between said first and second ends, said optical resonator having an optical whispering-gallery mode and being optically coupled to said optical path through an evanescent field to excite said optical whispering-gallery mode;
    an optical receiver arranged to be optically coupled to said second end of said optical path,
    wherein said optical source is frequency locked to a resonance frequency of said optical resonator and provides light sufficiently intense to provide four-wave mixing while being coupled with said optical resonator to generate a comb spectrum received by said optical receiver, and
    wherein said comb spectrum provides characteristic changes of the optical resonator at the resonance frequency in the presence of a substance in contact with said optical resonator to provide detection and characterization of said substance.

2. The label-free detection and characterization system according to claim 1, wherein said optical source comprises:
    a laser; and
    an optical amplifier arranged at least one of between said laser and said first end of said optical path or integral with said optical path along a portion thereof.

3. The label-free detection and characterization system according to claim 1, wherein said optical receiver comprises:
    an optical detector, and
    an optical filter or grating arranged between said second end of said optical path and said optical detector,
    wherein said optical filter or said grating substantially blocks or attenuates light from reaching said detector at a transmitting wavelength from said laser.

4. The label-free detection and characterization system according to claim 3, wherein said optical filter is a notch filter.

5. The label-free detection and characterization system according to claim 1, wherein said substance is at least one of a molecule, a virus, a portion of a virus, a biological cell, a portion of a biological cell, a microorganism, a portion of a microorganism, a chemical compound, a protein, a portion of a protein, or a particle.

6. The label-free detection and characterization system according to claim 1, further comprising a data processor arranged to be in electrical communication with said optical receiver.

7. The label-free detection and characterization system according to claim 6, further comprising a reference detection and characterization system arranged to be in electrical communication with said data processor, said reference detection and characterization system being free of contact with said substance.

8. The label-free detection and characterization system according to claim 7, said reference detection and characterization system comprising:
   a second optical source;
   a second optical path having a first end and a second end, said second optical path arranged to be optically coupled to said second optical source at said first end;
   a second optical resonator disposed proximate said second optical path along a side of said second optical path between said first and second ends, said second optical resonator having a second optical whispering-gallery mode and being optically coupled to said second optical path through an evanescent field to excite said second optical whispering-gallery mode;
   a second optical receiver arranged to be optically coupled to said second end of said second optical path,
   wherein said second optical source is frequency locked to a resonance frequency of said second optical resonator and provides light sufficiently intense to provide four-wave mixing while being coupled with said second optical resonator to generate a second comb spectrum received by said second optical receiver, and
   wherein said second comb spectrum provides a reference for comparison to the first mentioned comb spectrum.

9. The label-free detection and characterization system according to claim 8, wherein said second optical source comprises:
   a second laser; and
   a second optical amplifier arranged at least one of between said second laser and said first end of said second optical path or integral with said second optical path along a portion thereof.

10. The label-free detection and characterization system according to claim 9, wherein said second laser and the first-mentioned laser emit light at substantially the same wavelength, and
   wherein said second optical resonator and the first-mentioned optical resonator have substantially the same resonances.

11. The label-free detection and characterization system according to claim 8, wherein said second optical resonator is at least one of a ring, a goblet, a disk, a spherical, or micro-toroidal optical resonator.

12. The label-free detection and characterization system according to claim 8, wherein said second optical path is at least one of a free-space optical path, an optical waveguide, an optical fiber, an angled optical fiber or a prism.

13. The label-free detection and characterization system according to claim 8, wherein said second optical filter is a notch filter or grating.

14. The label-free detection and characterization system according to claim 8, wherein the first-mentioned optical whispering-gallery mode and said second optical whispering-gallery mode are close in resonance.

15. The label-free detection and characterization system according to claim 1, wherein said optical resonator is at least one of a disk, a goblet, spherical, a ring, or a microtoroidal optical resonator.

16. The label-free detection and characterization system according to claim 1, wherein said optical path is at least one of a free-space optical path, an optical waveguide, an optical fiber, an angled optical fiber or a prism.

17. The label-free detection and characterization system according to claim 1, wherein the substance is a protein.

18. The label-free detection and characterization system according to claim 1, wherein the substance is ribonucleic acid (RNA) or deoxynucleic acid (DNA).

19. The label-free detection and characterization system according to claim 1, wherein the optical resonator comprises a microtoroidal structure having nanoparticles attached to a surface of the microtoroidal structure.

20. The label-free detection and characterization system according to claim 19, wherein the nanoparticles are gold or silver nanorods or nanoshells attached to the surface of the microtoroidal structure to enhance sensitivity of detection and characterization of the substance.

* * * * *